(12) United States Patent
Jordan et al.

(10) Patent No.: US 6,302,688 B1
(45) Date of Patent: Oct. 16, 2001

(54) ORTHODONTIC APPLIANCE WITH SELF-RELEASING LATCH

(75) Inventors: Russell A. Jordan, Rancho Cucamonga; Ming-Lai Lai; John S. Kelly, both of Arcadia; Evangelos Georgakis, Altaloma, all of CA (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 09/405,751

(22) Filed: Sep. 27, 1999

(51) Int. Cl.[7] .................................................. A61C 3/00
(52) U.S. Cl. .................................................................. 433/8
(58) Field of Search .................................. 433/11, 10, 9, 433/8

(56) References Cited

U.S. PATENT DOCUMENTS

| | | |
|---|---|---|
| 1,991,047 * | 2/1935 | Boyd et al. ............................. 433/11 |
| 2,368,851 * | 2/1945 | Laskin ..................................... 433/11 |
| 3,052,027 | 9/1962 | Wallshein . |
| 3,084,437 | 4/1963 | Neger . |
| 3,327,393 | 6/1967 | Brader . |
| 3,464,112 * | 9/1969 | Silverman et al. ..................... 433/11 |
| 3,464,113 * | 9/1969 | Siverman et al. ..................... 433/11 |
| 3,724,074 | 4/1973 | Wallshein . |
| 3,772,787 | 11/1973 | Hanson . |
| 4,103,423 | 8/1978 | Kessel . |
| 4,149,314 | 4/1979 | Nonnenmann . |
| 4,171,568 | 10/1979 | Forster . |
| 4,197,642 | 4/1980 | Wallshein . |
| 4,248,588 | 2/1981 | Hanson . |
| 4,260,375 | 4/1981 | Wallshein . |
| 4,492,573 | 1/1985 | Hanson . |
| 4,496,318 | 1/1985 | Connelly, Jr. . |
| 4,551,094 | 11/1985 | Kesling . |
| 4,559,012 | 12/1985 | Pletcher . |
| 4,698,017 * | 10/1987 | Hanson ................................... 433/11 |
| 4,712,999 | 12/1987 | Rosenberg . |
| 4,725,229 | 2/1988 | Miller . |
| 4,846,681 | 7/1989 | Mourany et al. . |
| 5,174,754 * | 12/1992 | Meritt ..................................... 433/10 |
| 5,269,681 | 12/1993 | Degnan . |
| 5,322,435 | 6/1994 | Pletcher . |
| 5,356,289 | 10/1994 | Watanabe . |
| 5,466,151 | 11/1995 | Damon . |
| 5,474,445 | 12/1995 | Voudouris . |
| 5,516,284 | 5/1996 | Wildman . |
| 5,562,444 | 10/1996 | Heiser et al. . |
| 5,630,715 | 5/1997 | Voudouris . |
| 5,630,716 | 5/1997 | Hanson . |
| 5,685,711 | 11/1997 | Hanson . |
| 5,711,666 | 1/1998 | Hanson . |
| 5,857,849 | 1/1999 | Kurz . |
| 5,857,850 | 1/1999 | Voudouris . |
| 5,863,199 | 1/1999 | Wildman . |
| 5,890,893 | 4/1999 | Heiser . |
| 5,908,293 | 6/1999 | Voudouris . |
| 5,913,680 | 6/1999 | Voudouris . |
| 5,967,773 | 10/1999 | Roman et al. . |
| 5,971,753 | 10/1999 | Heiser . |
| 6,168,428 | 1/2001 | Voudouris . |

OTHER PUBLICATIONS

Voudouris, John C. "Seven Clinical Principles of Interactive Twin Mechanisms", *Journal Clinical Orthodontics, Inc.* 1997, vol. XXXI, No. 1, pp. 55–65.

* cited by examiner

*Primary Examiner*—Todd E. Manahan
(74) *Attorney, Agent, or Firm*—James D. Christoff

(57) ABSTRACT

An orthodontic appliance such as a bracket or buccal tube has a latch for retaining an archwire in an archwire slot. The latch releases the archwire from the archwire slot whenever the archwire exerts a force in a generally buccolabial direction on the appliance that exceeds a certain minimum value. The minimum value is less than about one-half of the force required in the same direction to debond the appliance from the tooth, and thus reduces the likelihood that the appliance will unintentionally debond from the tooth during the course of orthodontic treatment.

70 Claims, 13 Drawing Sheets

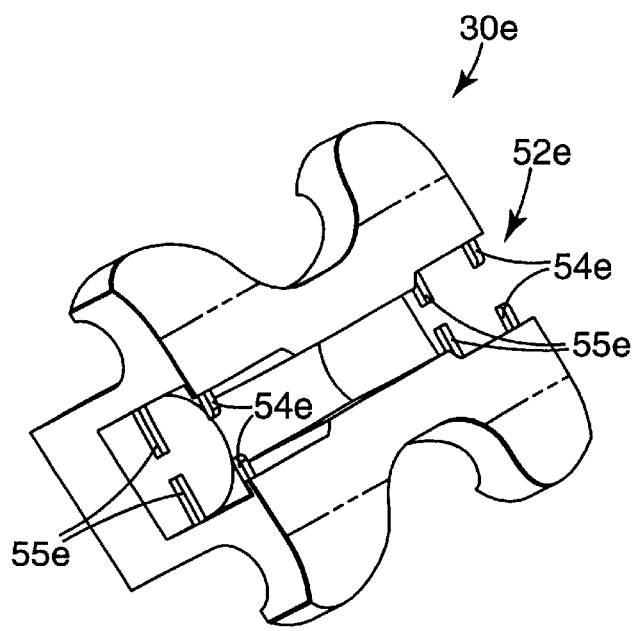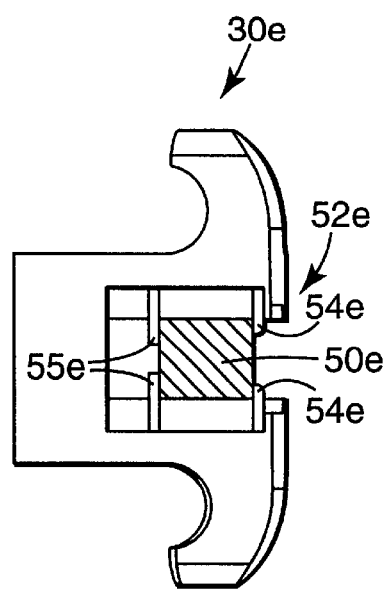
Fig. 10  Fig. 11
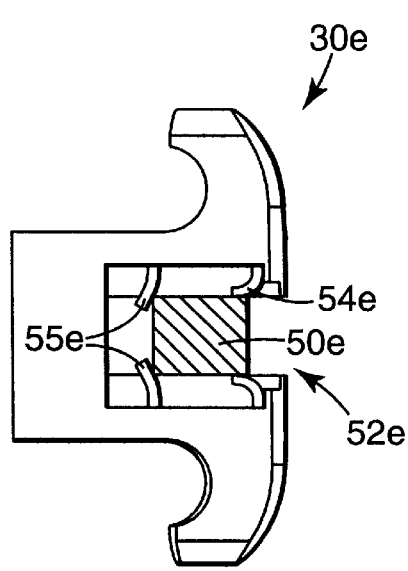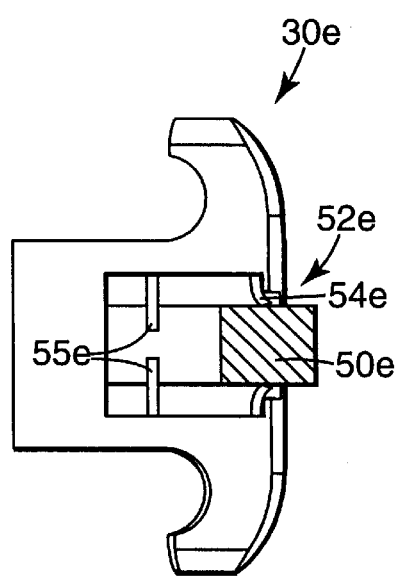
Fig. 12  Fig. 13

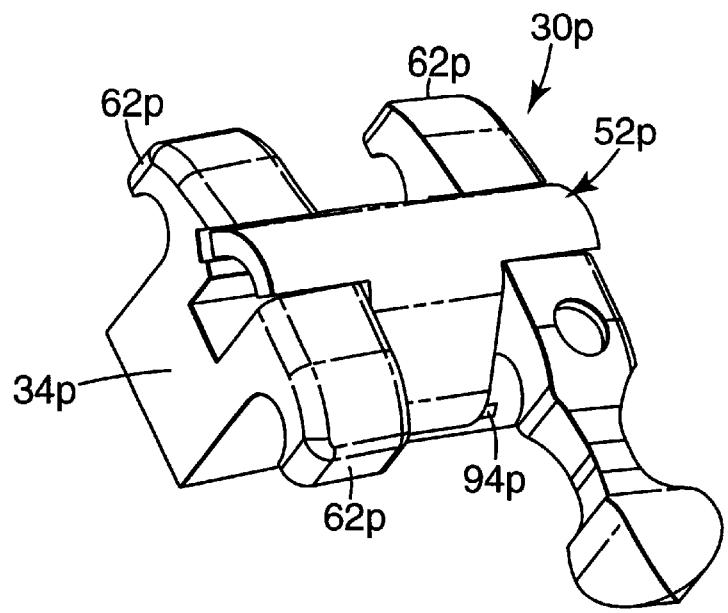
Fig. 28
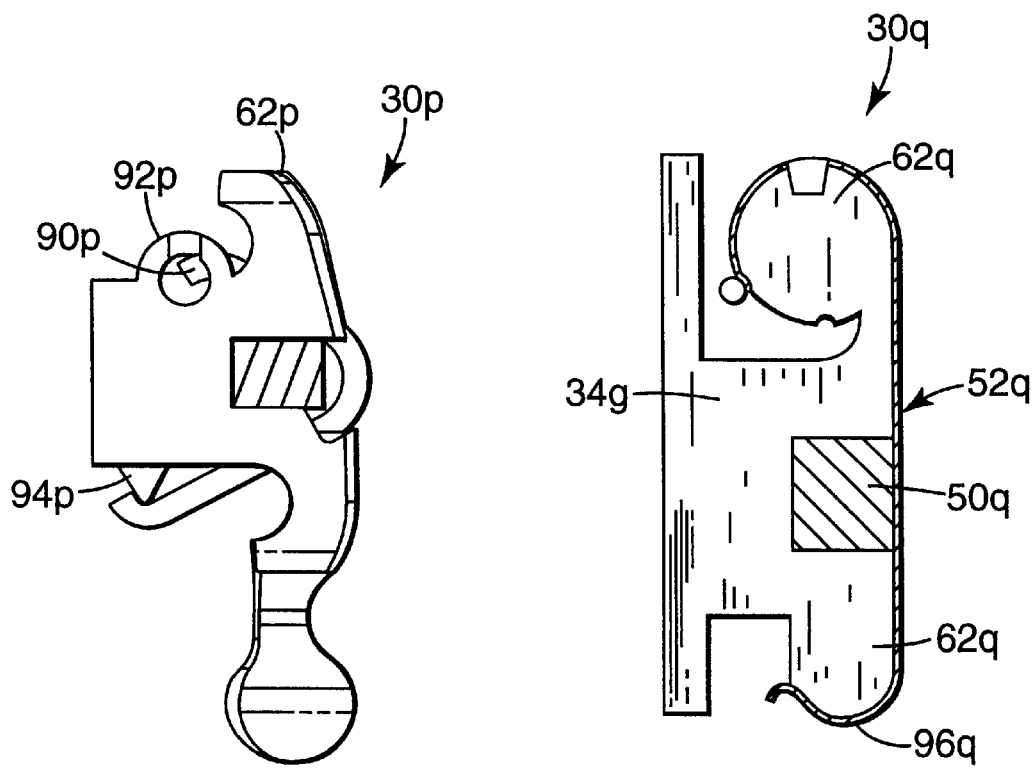
Fig. 29   Fig. 30

ORTHODONTIC APPLIANCE WITH SELF-RELEASING LATCH

BACKGROUND OF THE INVENTION

1. Field of the Invention

This invention broadly relates to an appliance used in orthodontic treatment. More particularly, the present invention relates to an orthodontic appliance such as a bracket or buccal tube having a releasable latch for releasably retaining an archwire in an archwire slot of the appliance.

2. Description of the Related Art

Orthodontic therapy is a specialized type of treatment within the field of dentistry, and involves movement of malpositioned teeth to orthodontically correct locations. Orthodontic treatment often improves the patient's occlusion and typically enhances the aesthetic appearance of the teeth.

Many types of orthodontic treatment programs involve the use of a set of tiny appliances and wires that are commonly known collectively as "braces". During such treatment programs, small appliances known as brackets are fixed to the patient's anterior, cuspid and bicuspid teeth, and an archwire is inserted into a slot of each bracket. The archwire forms a track to guide movement of the teeth to orthodontically correct locations. End sections of the archwires are typically captured in tiny appliances known as buccal tubes that are fixed to the patient's molar teeth.

Many types of orthodontic brackets have archwire slots that are open on one side for insertion of the archwire, and bounded on remaining sides by walls or other structure. Brackets that are intended to be bonded to the patient's front tooth surfaces often have archwire slots that are open either on a buccolabial side (i.e., a side facing the patient's cheeks or lips) or an occlusal side (i.e., a side facing the outer tips of the teeth) of the archwire slot. Some brackets, however, are intended to be fixed to the lingual side of the patient's teeth (i.e., the side of the teeth facing the patient's tongue) and in that instance typically have an archwire slot that is open on a lingual side or on an occlusal side.

Many orthodontists use ligatures to connect the archwire to the brackets and to urge the archwire into an orientation of seating engagement in the archwire slot. One type of commercially available orthodontic ligature is a small, elastomeric O-ring. Orthodontic O-rings are installed by stretching the O-ring around small wings (known as "tiewings") that are connected to the bracket body on the gingival side (i.e., the side facing the patient's gingiva or gums) and on the occlusal side of the archwire slot. Once installed, the O-ring ligature extends around the tiewings as well as over the labial side of the archwire and urges the archwire toward a fully seated position in contact with a lingual wall of the archwire slot.

Metal ligatures, such as ligatures made of stainless steel, are also used to retain archwires in archwire slots of brackets. Metal ligatures are typically made of a short section of initially straight wire. During installation, the wire ligature is hooked around the tiewings and extended over the labial side of the archwire. End sections of the ligature are then twisted together to form a loop to retain the ligature in place.

Unfortunately, some orthodontists are not entirely satisfied with elastomeric and metal ligatures. Such ligatures are somewhat time-consuming to install, both during initial installation and also during reinstallation whenever replacement of the archwire or ligatures is desired. As can be appreciated, a savings in the amount of time needed for ligation can help to reduce the total time that the practitioner must spend with the patient and consequently aid in reducing the overall costs of orthodontic treatment.

Other disadvantages are also associated with elastomeric and metal ligatures. For example, there have been reports that certain polyurethane elastomeric ligatures have exhibited deformation and force decay during the course of treatment. In some instances, elastomeric ligatures are stained by food and beverages consumed by the patient and become somewhat unsightly. Metal ligatures often have sharp ends that may retain plaque and food debris and also may increase the risk of infection.

In an effort to overcome the problems associated with conventional ligatures, a variety of orthodontic brackets have been proposed having various types of latches for coupling the archwire to the bracket. Such brackets are also known as self-ligating brackets. The latch comprises a clip, spring member, cover, shutter, bail or other structure that is connected to the bracket body for retaining an archwire in the archwire slot.

Examples of self-ligating orthodontic brackets having generally U-shaped ligating latch clips are described in U.S. Pat. Nos. 3,772,787, 4,248,588 and 4,492,573. In general, the clip of such brackets is slidably mounted on the bracket body, and a dental explorer or other small-tipped dental tool is used to move the clip relative to the body when needed in order to open or close the archwire slot. A self-ligating bracket known as the "Speed" brand bracket also has a movable, generally U-shaped clip for ligating the archwire to the bracket.

Other types of self-ligating brackets have latches that resemble swinging shutters or closures that pivotally move between a slot-open and a slot-closed position. For example, U.S. Pat. No. 4,712,999 has a rotatable cover plate that is pivotally connected at one end to a tiewing of the bracket along one side of the slot, and is releasably engagable at the other end with a tiewing that is located along the opposite side of the archwire slot. Other orthodontic brackets with swinging latches are described in U.S. Pat. Nos. 4,103,423, 5,516,284 and 5,685,711.

U.S. Pat. Nos. 4,371,337 and 4,559,012 describe self-ligating orthodontic brackets having latches that rotate about the longitudinal axis of the archwire slot. The latch of these references has a somewhat cylindrical shape and is rotatably received in a mating, cylindrical channel, and an outwardly extending arm is provided to assist in rotatably moving the latch between a slot-open and a slot-closed position.

A self-ligating orthodontic bracket that is described in U.S. Pat. No. 5,711,666 has a latch that comprises a flexible flat spring member. One end of the spring member is fixed to the bracket body on one side of the archwire slot, and the opposite end of the spring member has notches that releasably engage latch sears or catches when the spring member is moved to a slot-closed position. To open the slot, the notches are disengaged from the catches and the spring member is bent to an orientation sufficient to enable the archwire to be removed from the archwire slot.

Other types of self-ligating orthodontic brackets have latches that comprise essentially flat plates that are slidable between a slot-open and a slot-closed position. Examples of such construction are shown in U.S. Pat. Nos. 5,094,614, 5,322,435 and 5,613,850. In general, the sliding latches described in those references move in upright channels that are located buccolabially of the archwire slot.

Another type of self-ligating bracket that has been proposed in the past has a latch that is made of a section of wire material that functions similar to a bail. The orthodontic brackets described in U.S. Pat. Nos. 4,149,314, 4,725,229 and 5,269,681 have wire-like latches that swing between a slot-closed position and a slot-open position. The orthodontic bracket described in U.S. Pat. No. 4,260,375 has a wire latch that is slidable between a slot-open and a slot-closed position.

Many practitioners prefer self-ligating orthodontic brackets over brackets that are not self-ligating because the need to ligate each bracket with an initially separate elastomeric O-ring or a metal ligature wire can be avoided. However, conventional selfligating orthodontic brackets are not entirely satisfactory because of the lack of optimal control over movement of the underlying teeth. During the course of treatment, it may be necessary to shift each tooth relative to adjacent teeth in order to provide an aesthetically pleasing result at the conclusion of treatment. Precise control over movement of the teeth is desirable so that each tooth can be shifted as needed to its exact, intended orientation and in proper orthodontic relation relative to other teeth in the oral cavity.

In general, there are three types of tooth movement that are important to orthodontic practitioners. Tipping movement is one such type of movement, and may be defined as pivotal movement of the long axis of a tooth in a mesial-distal direction. Another movement is torque movement, and can be defined as pivotal movement of the long axis of a tooth in a buccal-lingual direction. The third type of tooth movement is rotational movement, and can be defined as rotational movement of a tooth about its long axis. Preferably, the appliances selected by the practitioner for use provide precise control over movement of the associated teeth for each type of tooth movement.

One problem that has been noted in connection with conventional direct-bonded appliances, including self-ligating brackets, is the possibility that such brackets may spontaneously debond from the patient's tooth when the teeth are severely maloccluded. For example, if one of the patient's teeth is located a relatively large distance in a lingual direction relative to adjacent teeth in the dental arch, the archwire must be deformed a significant distance in order to engage the archwire slot of the bracket. In such instances, the inherent tendency of the archwire to return to its normally arch-shaped configuration will cause the archwire to exert a substantial force on the appliance bonded to the severely maloccluded tooth. Unfortunately, the bracket may then debond from the tooth if the archwire exerts a force that is larger than the force required to debond the bracket in the same direction.

Brackets that spontaneously debond from teeth represent a waste of time and expense for both the practitioner and the patient, and are best avoided if at all possible. Once a bracket has unintentionally debonded from a tooth, the archwire is removed from the slot of each bracket and the tooth is cleaned and etched in preparation to receive another bracket. If the debonding occurs outside of the practitioner's office, the orthodontic treatment of that tooth is interrupted until such time as the patient returns to the practitioner's office for replacement of the bracket.

In the past, practitioners have sometimes used relatively small-diameter archwires in the initial stages of orthodontic treatment when one or more teeth in the dental arch are severely maloccluded. Such archwires provide relatively little force to the appliances, and as a consequence reduce the likelihood that appliances that are directly bonded to severely maloccluded teeth will spontaneously debond during the course of treatment. Unfortunately, the use of such small-diameter archwires somewhat retards the progress of treatment in comparison to the use of larger diameter archwires, since the force provided by the archwire to all of the teeth is somewhat reduced.

While many types of self-ligating orthodontic appliances have been proposed in the past, there remains a continuing need to improve the state of the art so that the treatment program can be completed in prompt fashion, the duration of the patient's appointments can be shortened and the practitioner's efficiency is increased. For example, it would be desirable to provide a self-ligating appliance that reduces the time needed for installation of an archwire in comparison to conventional self-ligating brackets, so that the time of both the practitioner as well as the patient to complete the installation procedure can be reduced. Moreover, it would be desirable if such an appliance could provide precise control over movement of the associated tooth while also facilitating movement of the tooth to its desired ultimate location.

SUMMARY OF THE INVENTION

The present invention is directed toward an orthodontic appliance such as a bracket or buccal tube having features that represent significant advantages over known self-ligating appliances. In one aspect of the invention, the appliance has a latch for releasably retaining an archwire in the archwire slot. The latch releases the archwire from the archwire slot whenever the archwire exerts a force on the appliance that exceeds a certain minimum value. The minimum value is significantly less than the force required in the same direction to debond the appliance from the tooth, and consequently helps ensure that the appliance will not spontaneously debond from the tooth during the course of treatment.

The self-releasing latch of the present invention is also beneficial in that the maximum force exerted by the appliance on the patient's tooth can be limited to a pre-selected value, which in some instances may be lower than the force required to debond the appliance from the tooth. As a result, the amount of any pain experienced by the patient due to forces exerted by the appliance is also limited. The force limiting latch also helps ensure that undue force is not exerted on root portions of the associated tooth so that blood vessels adjacent the root portions are not significantly compressed and blood in the vessels continues to freely circulate to facilitate bone regeneration.

Another aspect of the invention is directed toward a self-ligating appliance having a latch that is movable to a slot-open position to enable passage of an archwire into the slot by pressing the archwire against the latch in a lingual direction. The occlusal side and the gingival side of the archwire slot are immovable relative to each other, and thereby provide good control over movement of the appliance and the associated tooth whenever torquing, tipping, intruding or extruding of the tooth is desired.

Another aspect of the present invention is directed toward a self-ligating orthodontic appliance having a latch that is movable to a slot-open position by pressing the archwire against the latch in a lingual direction. The lingual side of the archwire slot moves in a generally lingual direction as the archwire is pressed into the archwire slot.

Other aspects of the invention relate to a self-ligating orthodontic appliance having a latch that comprises at least one clip. The clip provides certain advantages when manufacturing the appliance, and also enhances the practitioner's control over movement of the associated teeth.

In more detail, the present invention is directed in one embodiment toward an orthodontic appliance that comprises a base for bonding the appliance to a tooth and a body extending from the base. The appliance also includes an archwire slot extending across the body in a generally mesial-distal direction. The appliance additionally includes a latch connected to the body for releasably retaining an archwire in the archwire slot. The latch releases the archwire from the archwire slot in a generally buccolabial direction whenever the archwire exerts a force greater than about 2.3 kg in the same direction on the appliance.

The present invention is directed in another embodiment toward an orthodontic appliance comprising a base for bonding the appliance to a tooth and a body extending from the base. The appliance also includes an archwire slot extending across the body in a generally mesial-distal direction. The appliance additionally includes a latch connected to the body for releasably retaining an archwire in the archwire slot. The latch releases the archwire from the archwire slot in a generally buccolabial direction whenever the archwire exerts a force in the same direction on the appliance that exceeds a certain minimum value. The minimum value is less than about one-half of the force required in the same direction to debond the appliance from the tooth.

Another embodiment of the present invention is also directed toward an orthodontic appliance that comprises a base for bonding the appliance to a tooth and a body extending from the base. An archwire slot extends across the body in a generally mesial-distal direction and has an occlusal side, a gingival side and a lingual side. The appliance also includes a latch connected to the body for releasably retaining an archwire in the archwire slot. The latch is movable to a slot-open position to enable passage of the archwire into the slot by pressing the archwire against the latch in a direction toward the lingual side of the archwire slot. The occlusal side and the gingival side of the archwire slot are stationary relative to each other as the latch is moved to a slot-open position.

The present invention is also directed in another embodiment to an orthodontic appliance that comprises a base for bonding the appliance to a tooth and a body extending from the base. An archwire slot extends across the body in a generally mesial-distal direction and has an occlusal side, a gingival side and a lingual side. The appliance also includes a latch connected to the body for releasably retaining an archwire in the archwire slot. The latch is movable to a slot-open position to enable passage of the archwire into the slot by pressing the archwire against the latch in a direction toward the lingual side of the archwire slot. The lingual side of the archwire slot is movable in a generally lingual direction as the archwire is pressed into the archwire slot.

Another embodiment of the present invention is directed to an orthodontic appliance that comprises a base for bonding the appliance to a tooth, and a body extending from the base having a mesial side and a distal side. The appliance includes an archwire slot extending across the body in a generally mesial-distal direction. The appliance further includes a latch movable between a slot-closed position for retaining an archwire in the archwire slot and a slot-open position for releasing the archwire from the archwire slot. The latch comprises a mesial clip that is located mesially of the mesial side and a distal clip that is located distally of the distal side.

In another embodiment, the present invention is directed toward an orthodontic appliance that also includes a base for bonding the appliance to a tooth and a body extending from the base. An archwire slot extends across the body in a generally mesial-distal direction. The appliance also includes a latch movable between a slot-closed position for retaining an archwire in the archwire slot and a slot-open position for releasing the archwire from the archwire slot. The latch comprises at least one assembly of a sleeve and a resilient clip extending through the sleeve, and each sleeve is fixed to the body.

These and other aspects of the invention are described in more detail below and are illustrated in the accompanying drawings.

BRIEF DESCRIPTION OF THE DRAWINGS

FIG. 10 is a perspective view of an orthodontic appliance constructed in accordance with yet another embodiment of the invention;

FIG. 11 is an end elevational view of the orthodontic appliance shown in FIG. 10 and looking toward a mesial side of the appliance, and additionally illustrating in cross-section an archwire that is received in an archwire slot of the appliance;

FIG. 12 is a view somewhat similar to FIG. 11 but showing an example of how the appliance appears as the archwire is moved into the archwire slot;

FIG. 13 is a view somewhat similar to FIG. 11 but showing an example of how the archwire appears as the archwire is released from the archwire slot;

FIG. 28 is a perspective view of an orthodontic appliance according to a further embodiment of the invention;

FIG. 29 is an end elevational view of the appliance depicted in FIG. 28 and looking toward a mesial side of the appliance, and additionally illustrating an archwire that is received in an archwire slot of the appliance;

FIG. 30 is an end elevational view of an orthodontic appliance that is constructed according to yet another embodiment of the invention;

DETAILED DESCRIPTION OF THE PREFERRED EMBODIMENTS

Figure 1:
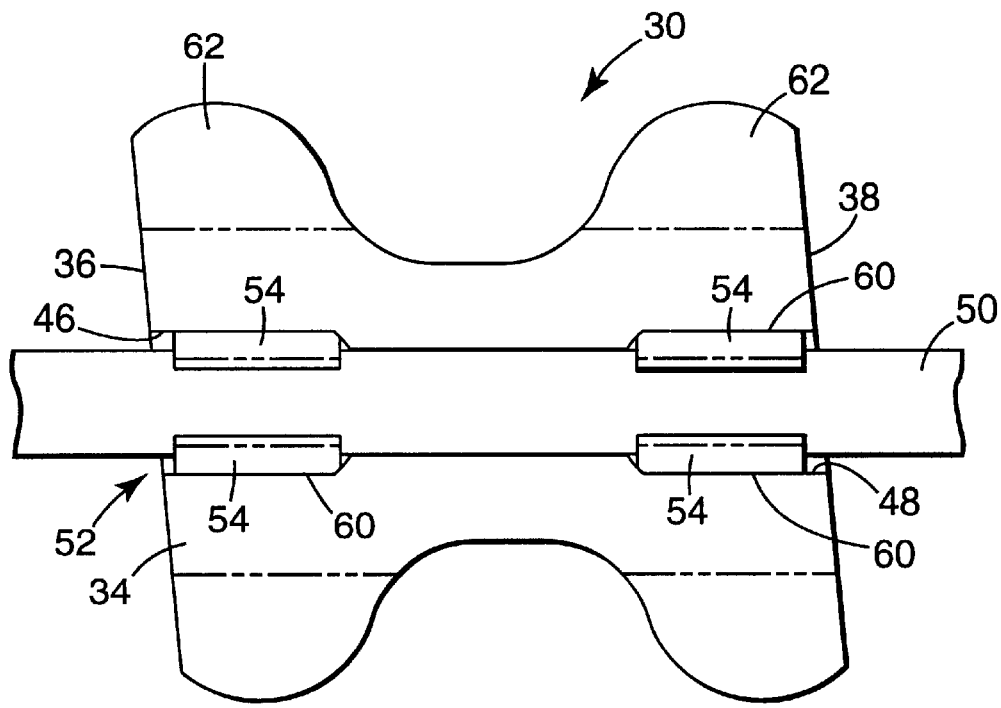
FIG. 1 is a front elevational view looking in a lingual direction toward an orthodontic appliance constructed in accordance with one embodiment of the present invention along with an orthodontic archwire that is received in an archwire slot of the appliance.

An orthodontic appliance constructed in accordance with one embodiment of the present invention is illustrated in FIGS. 1–5 and is broadly designated by the numeral 30. The appliance 30 in this instance is an orthodontic bracket adapted to be secured to the buccolabial surface of a patient's tooth. Alternatively, the appliance could be a buccal tube or any other orthodontic appliance that is adapted to receive an archwire for controlling movement of the teeth during the course of orthodontic therapy.

The appliance 30 includes a base 32 for bonding the appliance 30 directly to the patient's tooth enamel by use of an adhesive. Preferably, the base 32 has a concave compound contour that matches the convex compound contour of the patient's tooth surface. Optionally, the base 32 may be provided with grooves, particles, recesses, undercuts, a chemical bond enhancement material or any other material or structure or any combination of the foregoing that facilitates bonding the appliance 30 directly to the patient's tooth enamel.

A body 34 extends outwardly from the base 32 in a generally buccolabial direction. The body 34 includes an outermost mesial side 36 as well as an outermost distal side 38. In the embodiment shown, the body 34 is integral with the base 32, although in this and in other embodiments other constructions are possible. For example, the base 32 could be comprised of a mesh screen or other bond enhancement structure that is connected by welding, brazing, adhesive or other means to the lingual side of the body 34, and could extend past the body 34 in lateral directions (such as in occlusal-gingival directions).

An archwire slot 40 extends across the body 34 in a generally mesial-distal direction. The archwire slot 40 includes an occlusal side that is defined in part by a flat occlusal wall portion 42 that is fixed to the body 34. The archwire slot 40 also has a gingival side that is defined in part by a flat gingival wall portion 44 that is also fixed to the body 34. Alternatively, the wall portions 42, 44 could be curved, or part of ridges, bumps or other types of protrusions. The wall portions 42, 44 are immovable relative to each other and parallel to each other.

In the embodiment shown in FIGS. 1–5, the appliance 30 includes a mesial archwire slot relief area 46 and a distal archwire slot relief area 48. The relief areas 46, 48 are optional, but advantageously provide greater interbracket width and enhanced control over movement of the tooth as described in U.S. Pat. No. 4,531,911, the disclosure of which is incorporated by reference herein. The parallel wall portions 42, 44 are spaced apart a distance adapted to matingly engage occlusal and gingival sides respectively of an archwire 50 having a certain rectangular, cross-sectional configuration, so that precise control is afforded over tipping and torquing movement of the associated tooth.

The appliance 30 also includes a latch 52 that is connected to the body 34 for releasably retaining the archwire 50 in the archwire slot 40. In this embodiment, the latch 52 includes two pair of arm portions 54 as well as a spring member 56. The arm portions 54 are flat and connected to the body 34 in locations adjacent the archwire slot relief areas 46, 48, although other locations are also possible.

The arm portions 54 are resilient and can be deformed in either a lingual direction or a buccolabial direction. Suitable materials for the arm portions 54 include flat spring material made, for example, of stainless steel or of a shape memory alloy (such as nitinol). The arm portions 54 may be fixed to the body 34 by any suitable technique such as brazing or welding (including laser welding) or by use of fasteners or the like.

The spring member 56 extends along the length of the archwire slot 40 and is optionally made from an intially flat section of metallic material that is bent to an appropriate shape. In the embodiment shown in the drawings, the spring member 56 has a middle portion that is received in a sleeve coupling 58. In turn, the coupling 58 is secured to the body 34 adjacent a central area of the lingual side of the archwire slot 40.

Suitable materials for the spring member 56 include stainless steel alloys as well as shape-memory alloys. If the spring member 56 and the body 34 are both made of stainless steel, the middle portion of the spring member 56 can simply be brazed or welded to the body 34 and the sleeve 58 can be omitted. On the other hand, if the spring member 56 is made of a shape-memory alloy such as nitinol and the body 34 is of stainless steel, it may be difficult to weld or braze the nitinol spring member 56 to the stainless steel body 34. In that instance, the sleeve 58 when made of stainless steel can be readily brazed or welded to the body 34 and will provide a means for securely connecting the spring member 56 to the body 34.

The spring member 56 includes an outermost mesial portion and an outermost distal portion. The mesial and distal portions define the lingual side of the archwire slot 40 and rest against a lingual wall of the archwire 50 when the latter is fully seated in the archwire slot 40. Preferably, the spring member 56 is constructed so that the mesial and distal portions of the spring member 56 engage the lingual side of the archwire 50 and urge the archwire 50 into contact with a lingual surface of the arm portions 54.

Figure 4:
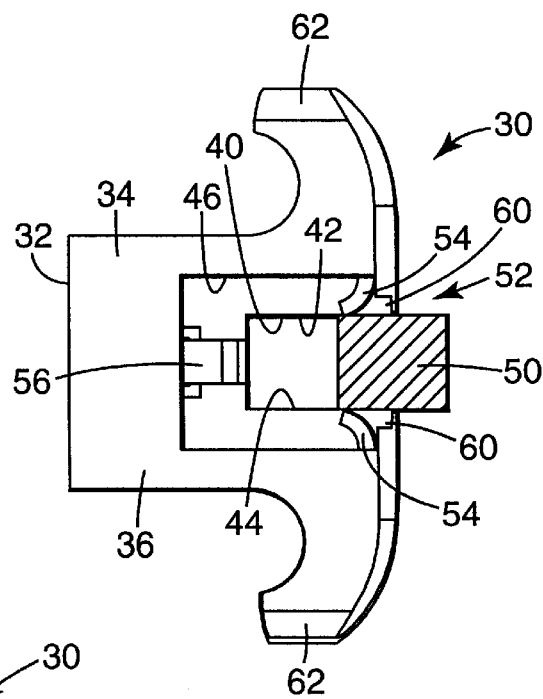
FIG. 4 is a view somewhat similar to FIG. 3 but showing an example of how the latch appears as the archwire is pushed into the archwire slot.

FIG. 4 is an exemplary illustration of how the appliance 30 might appear during the time that the archwire 50 is inserted into the archwire slot 40. As shown, the arm portions 54 deflect inwardly in a generally lingual direction to a degree sufficient to provide clearance and enable passage of the archwire 50 into the archwire slot 40. The arm portions 54 in this embodiment deflect inwardly in an arc about a reference axis that extends parallel to the archwire slot 40, although other constructions are possible. Advantageously, the arm portions 54 self-deflect inwardly to such a slot-open position as the practitioner presses the archwire 50 against the arm portions 54. As a result, no hand instruments are necessary to move the latch 52 to a slot-open position.

Once the archwire 50 is received in the archwire slot 40 a sufficient distance to engage the mesial and distal portions of the spring member 56, continued movement of the archwire 50 in a lingual direction will deform the spring member 56 and enable the mesial and distal portions to be deflected in a lingual direction. Additional movement of the archwire 50 in a lingual direction will then cause the spring member 56 to somewhat flatten and approach a generally planar configuration until such time as the buccolabial side of the archwire 50 has been moved past the outer, facing ends of the arm portions 54.

Figure 2:
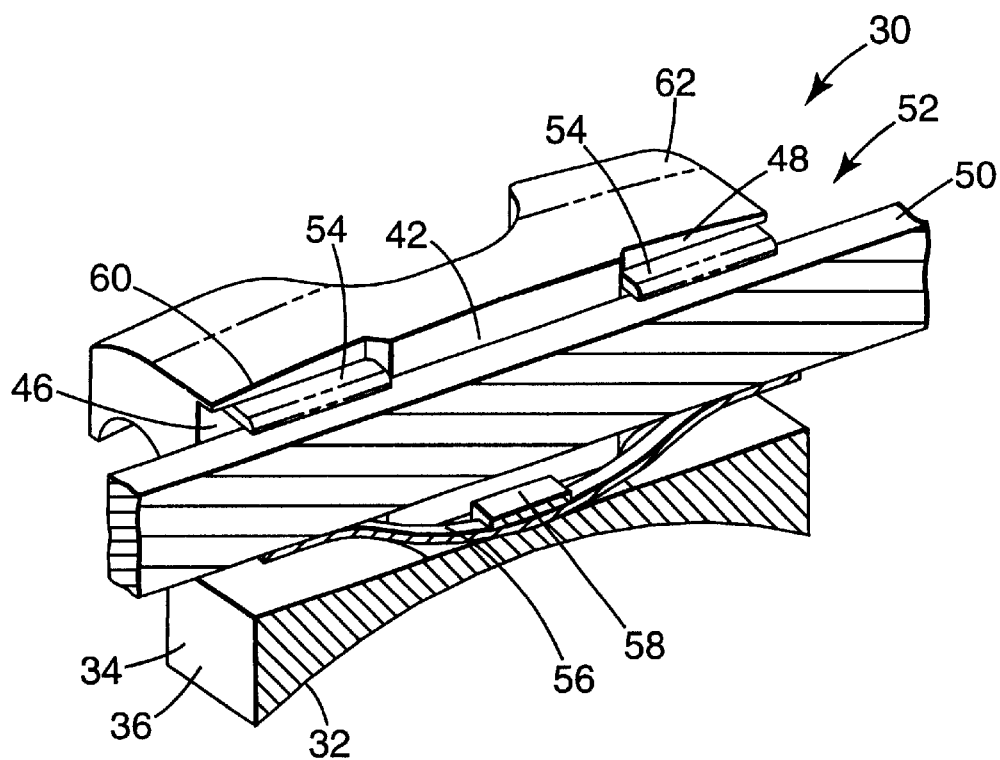
FIG. 2 is a cross-sectional perspective view of the appliance shown in FIG. 1 and illustrating in more detail a latch for releasably retaining the archwire in the archwire slot.
Figure 3:
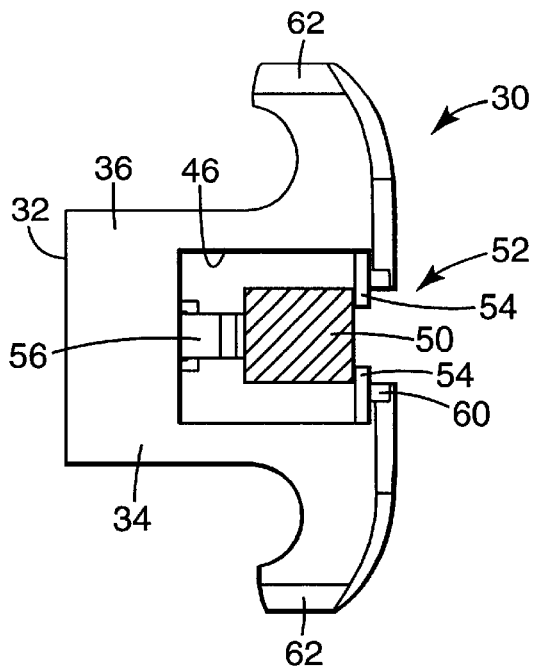
FIG. 3 is an end elevational view looking toward a mesial side of the appliance and the archwire of FIGS. 1 and 2.

Once the buccolabial side of the archwire 50 is clear of the outer ends of the arm portions 54, the arm portions 54 self-deflect in a buccolabial direction and return to their normal shape as shown in FIGS. 1–3. At that time, pressure on the archwire 50 is released by the practitioner and the spring member 56 functions to urge the archwire 50 in a buccolabial direction and toward a position of contact with the lingual side of the arm portions 54. Thereafter, the archwire 50 cooperates with the appliance 30 to provide orthodontic therapy for the associated tooth bonded to the base 32.

Figure 5:
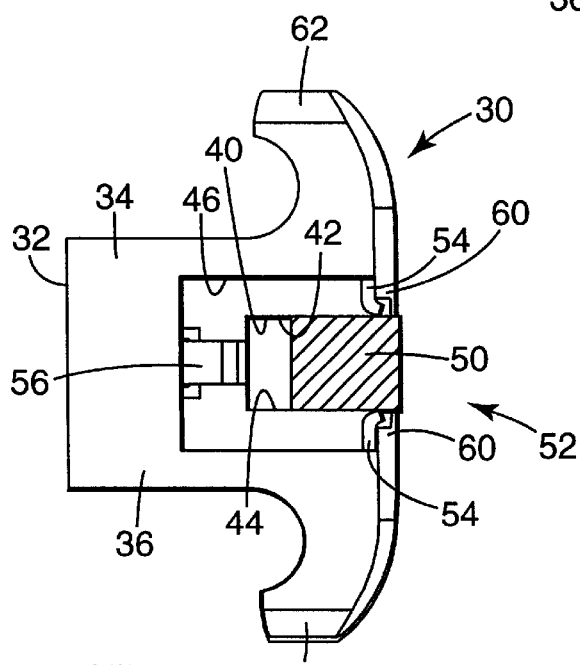
FIG. 5 is a view somewhat similar to FIG. 3 but showing an example of how the latch appears as the archwire is released from the archwire slot.

FIG. 5 is an exemplary illustration of how the appliance 30 might appear during release of the archwire 50 from the archwire slot 40. As shown, the arm portions 54 deflect outwardly to allow movement of the archwire 50 out of the archwire slot 40 in a generally buccolabial direction. The arm portions 54 deflect outwardly by bending in an arc about a reference axis extending parallel to the archwire slot 40, although other constructions are also possible.

Once the archwire 50 has moved in a buccolabial direction a distance sufficient to clear the outer ends of the arm portions 54, the archwire 50 disengages the appliance 30 and the arm portions 54 self-deflect to return to their normally straight, planar orientation as shown in FIGS. 1–3. Preferably, the arm portions 54 as well as the spring member 56 have sufficient resiliency to deflect and deform in the manner described a repeated number of times without exceeding the yield stress of the material of which they are made. As a result, the arm portions 54 and the spring member 56 will consistently return to their original shape and provide predictable results during the entire course of orthodontic therapy even though the latch 52 may open and close numerous times.

Preferably, the buccolabial side of the appliance 30 is provided with four shoulders 60, each of which extends partially over a respective one of the arm portions 54. Optionally, the shoulders 60 are integrally connected to the body 34, although other constructions are also possible. Preferably, the arm portions 54 are not fixed to the shoulders 60 so that the arm portions 54 can move away from the respective shoulders 60 in a lingual direction as the archwire 50 is inserted into the archwire slot 40.

The shoulders 60 provide a resistance to outward deflection (i.e., deflection in a generally buccolabial direction) of the arm portions 54 but provide no resistance to inward deflection (i.e., deflection in a generally lingual direction) of the arm portions 54. The shoulders 60 effectively shorten the length of the arm portions 54 available for outward bending movement, and effectively stiffen the arm portions 54 during outward movement. As a result, a greater force is needed to push the arm portions 54 outwardly and release the archwire 50 from the archwire slot 40 than the force required in the opposite direction to push the arm portions 54 inwardly and enable the archwire 50 to be inserted into the archwire slot 40.

The arm portions 54 deflect outwardly to a slot-open position as shown in FIG. 5 whenever the force exerted by the archwire 50 on the appliance 30 (specifically, in this embodiment whenever the force exerted by the archwire 50 on the arm portions 54) exceeds a certain minimum value. The minimum value is sufficiently high to prevent the archwire 50 from unintentionally releasing from the archwire slot 40 during the normal course of orthodontic treatment. As such, the archwire 50 can exert forces on the appliance 30 sufficient to carry out the treatment program and move the associated tooth as desired. The minimum value is preferably at least about 5 lbs. (2.3 kg), more preferably at least about 3 lbs. (1.4 kg) and most preferably at least about 1.5 lbs. (0.7 kg).

Whenever the force exerted by the archwire 50 on the appliance 30 exceeds the selected minimum value, the arm portions 54 self-deflect outwardly to release the archwire 50 from the archwire slot 40. For example, if the archwire 50 has a relatively large transverse cross-sectional area and is deflected from its normal shape a substantial distance in order to be inserted into the archwire slot 40 (as may occur when the tooth bonded to the appliance 30 is severely maloccluded and located a substantial distance from adjacent teeth), the arm portions 54 will deflect outwardly as soon as the archwire 50 is placed in the archwire slot 40 and pressure by the practitioner in a lingual direction on the archwire 50 is released. As a consequence, the arm portions 54 of the latch 52 substantially preclude the archwire 50 from exerting a force on the appliance 30 that is greater than the minimum value as mentioned above.

To determine the force to release the latch 52, a section of archwire is selected having an area in longitudinally transverse sections that is complemental to (i.e., substantially fills) the cross-sectional area of the archwire slot 40. Next, a sling is constructed and is connected to the archwire section closely adjacent but not in contact with the mesial side 36 and the distal side 38. Optionally, the sling is welded or brazed to the archwire section. Next, the sling is pulled away from the appliance 30 while the appliance 30 is held in a stationary position, taking care to ensure that the longitudinal axis of the archwire section does not tip relative to the longitudinal axis of the archwire slot 40. The force to release the latch 52 is determined by use of an Instron testing apparatus connected to the sling, using a crosshead speed of 0.5 in/min. (1.3 cm/min.).

Preferably, the minimum value for self-release (i.e., self-opening) of the latch 52 is substantially less than the force required in the same direction to debond the appliance 30 from the associated tooth. Preferably, the selected minimum value is less than about 8 lbs. (3.6 kg). Additionally, the minimum value for self-release of the latch 52 is preferably less than about one-half of the force required in the same direction to debond the appliance 30 from the associated tooth. For example, if the expected bond strength of the adhesive bond between the appliance 30 and the associated tooth is 16 lbs. in a buccolabial direction, the latch 52 is constructed to self-release the archwire 50 whenever the archwire 50 exerts a force in the same buccolabial direction on the appliance 30 that is somewhat greater than about 8 lbs. (3.6 kg).

The self-releasing latch 52 is a benefit to the practitioner, in that the likelihood of spontaneous debonding of the appliance 30 is substantially reduced. For example, if the practitioner attempts to place a relatively large archwire in the archwire slot 40 and the latch 52 self-releases as soon as the practitioner releases the archwire, the practitioner can then use an archwire with less stiffness in its place. As another example, if the archwire 50 is initially held in the archwire slot 40 by the arm portions 54 and the archwire 50 subsequently exerts a larger force on the appliance 30 (as may occur, for example, when the archwire 50 encounters a hard object such as when the patient is chewing relatively hard food), the arm portions 54 will deflect outwardly to their slot-open position to release the archwire 50 so that the appliance 30 does not debond from the tooth. Treatment can then be resumed by merely replacing the archwire 50 in the archwire slot 40 without the need to rebond the base 32 to the associated tooth.

Preferably, the distance between the opposed ends of each pair of arm portions 54 is less than the overall occlusal-gingival dimension of the smallest archwire expected to be used during the course of treatment. The archwire 50 need not fill the archwire slot 40 and flatly engage the wall portions 42, 44 in all instances. For example, a somewhat smaller wire, and perhaps a wire having a circular cross-sectional shape, may be used during a portion of the treatment program. The distance between the opposed ends of each pair of spring members 56 is preferably selected so that a variety of archwires of different cross-sectional configurations may be used in connection with the appliance 30.

When an archwire having a relatively large cross-sectional area is placed in the archwire slot 50, the deformable nature of the resilient spring member 56 provides active treatment and facilitates movement of the associated tooth while the appliance 30 moves along the archwire 40. During such movement, the resilient spring member 56 urges the archwire 50 in a direction toward the arm portions 54 and toward a position of flat contact with all four of such arm portions 54. As such, the spring member 56 helps to move the associated tooth to position selected by the practitioner, since the inherent bias of the spring member 56 contributes to the forces exerted on the associated tooth.

Optionally, the appliance 30 includes one or more tiewings or tiewing portions 62. The appliance 30 as illustrated has four tiewings portions 62, each of which is integrally connected to the body 34.

The tiewing portions 62 provide an alternative method of connecting the archwire 50 to the appliance 30. For example, if the archwire 50 cannot be fully inserted into the archwire slot 40 without undue force, the archwire 50 may be ligated to the appliance 30 by passing a ligature around one or more of the tiewing portions 62 as well as around a portion of the archwire 50 without fully seating the archwire 50 in the archwire slot 40. As the associated tooth moves toward a position of alignment with adjacent teeth and closer to the archwire slot 40 over a period of time, less force is needed to fully seat the archwire 50 in the archwire slot 40. At that time, the ligature may then be removed and the archwire 50 retained in the archwire slot 40 by means of the latch 52.

Figure 6:
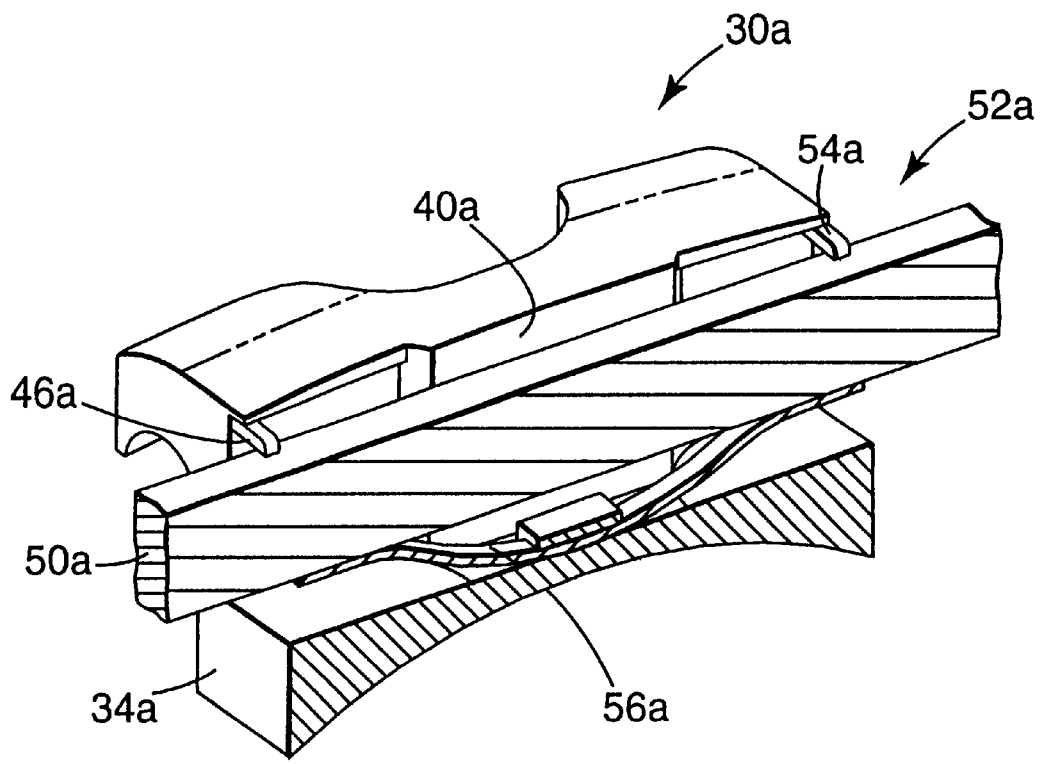
FIG. 6 is a view somewhat similar to FIG. 2 but showing an orthodontic appliance constructed in accordance with another embodiment of the invention.

An orthodontic appliance 30*a* that is constructed in accordance with another embodiment of the invention is shown in FIG. 6. The appliance 30*a* is essentially the same as the appliance 30 described above, except for the differences noted below.

The appliance 30*a* includes a latch 52*a* having four spaced apart arm portions 54*a*. The arm portions 54*a* are somewhat different than the arm portions 54, in that the arm portions 54*a* are narrower and optionally made of a section of wire material. Optionally, each arm portion 54*a* may be secured to the body 34*a* by drilling a small hole in the body 34*a* to receive a section of the arm portion 54*a*. The arm portions 54*a* may be secured in the holes by means of an interference fit, by welding or brazing, by an adhesive, by fasteners or by any other suitable means.

Although only two of the arm portions 54*a* are illustrated in FIG. 6, the latch 52*a* has four arm portions 54*a* that are arranged in opposed pairs in similar fashion to the arrangement of the arm portions 54 of the latch 52. Moreover, the latch 52*a* has a spring member 56*a* that is essentially the same as the spring member 56. In all other respects, the appliance 30*a* is identical to the appliance 30 described above.

Figure 6A:
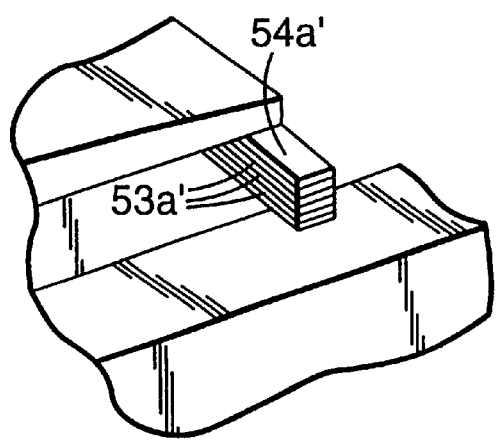
FIG. 6a is an enlarged cross-sectional perspective view of a portion of the appliance and archwire depicted in FIG. 6 but showing an alternative latch construction.

FIG. 6*a* illustrates an alternative arm portion 54*a*' that may be used if desired in place of the arm portions 54*a* depicted in FIG. 6. The arm portion 54*a*' as shown in FIG. 6*a* is made of a stack of discreet sections 53*a*' that move independently relative to each other. The stack may comprise 5, 10 or any other suitable number of sections 53*a*'. The use of discreet sections 53*a*' facilitates deflection of the arm portion 54*a*' in a labial or in a lingual direction when desired.

Figure 7:
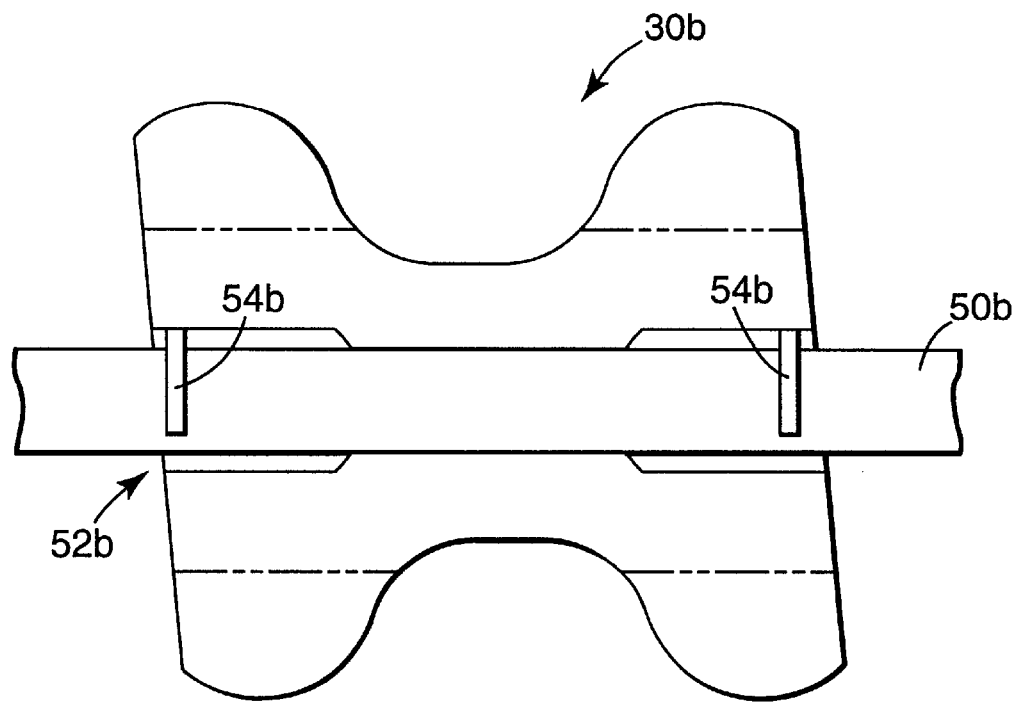
FIG. 7 is a view somewhat similar to FIG. 1 but illustrating an orthodontic appliance constructed in accordance with another embodiment of the invention.

An orthodontic appliance 30*b* according to another embodiment of the invention is shown in FIG. 7 in elevational view. The appliance 30*b* is similar to the appliance 30*a*, except for the differences noted below.

The appliance 30*b* has a latch 52*b* that includes two arm portions 54*b*. Each arm portion 54*b* extends across a labial side of an archwire 50*b* that is received in an archwire slot of the appliance 30*b*.

Preferably, each arm portion 54*b* extends across the labial side of the archwire 50*b* a distance that is greater than at least half of the occlusal-gingival dimension of the archwire 50*b*. In FIG. 7, the arm portions 54*b* are shown as descending in a gingival direction from an occlusal side of archwire slot relief areas, although as an alternative, the arm portions 54*b* could extend in an occlusal direction from a gingival side of each archwire slot relief area. The arm portions 54b may be made of a single, solid section of wire, or alternatively may each be made of a number of sections arranged in a stacked array similar to the arm portion 54a' illustrated in FIG. 6a.

Figure 8:
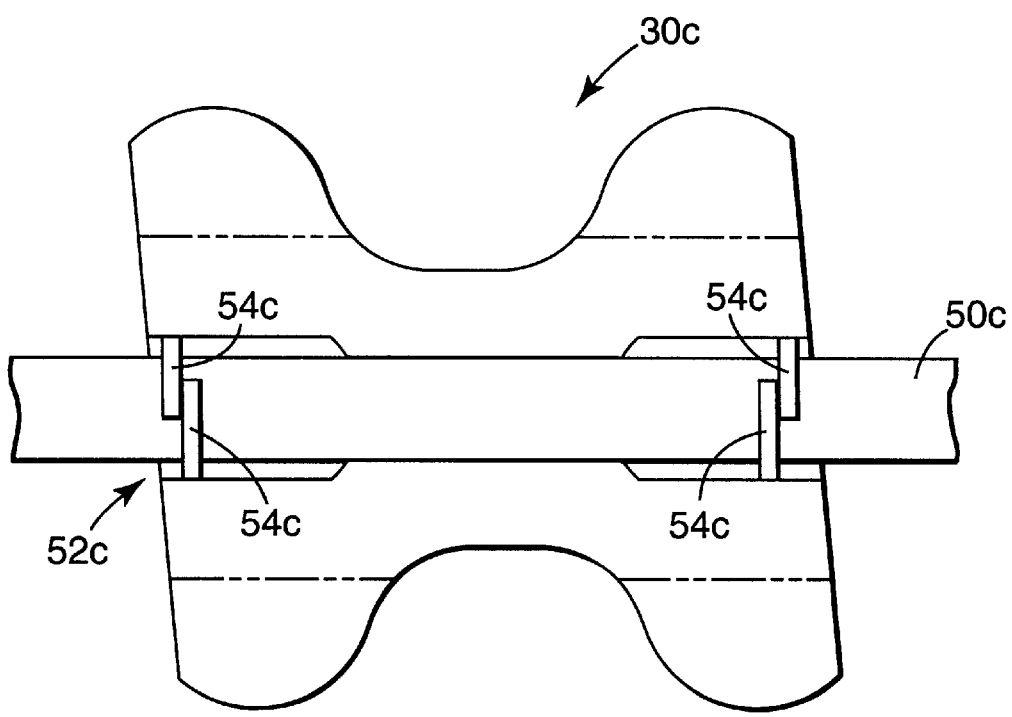
FIG. 8 is view somewhat similar to FIG. 1 but illustrating an orthodontic appliance constructed in accordance with yet another embodiment of the invention.

An orthodontic appliance 30c that is constructed in accordance with another embodiment of the invention is illustrated in FIG. 8. The appliance 30c is similar to the appliance 30a, except for the differences as set out below.

The appliance 30c includes a latch 52c having four arm portions 54c. The arm portions 54c are somewhat similar to the arm portions 54a, except that the arm portions 54c are somewhat longer and overlap each other. Additionally, the arm portions 54c that extend from an occlusal side of archwire slot relief areas are located laterally of arm portions 54c that extend from a gingival side of the archwire slot relief areas, although alternative constructions could be provided as well.

Optionally, and as shown in FIG. 8, each of the arm portions 54c extends a distance across a labial side of the archwire that is greater than one-half of the occlusal-gingival dimension of the labial side of the archwire. As another option, each arm portion 54c is made of a stack of discreet sections, similar to the sections 53a' as described above.

Figure 9:
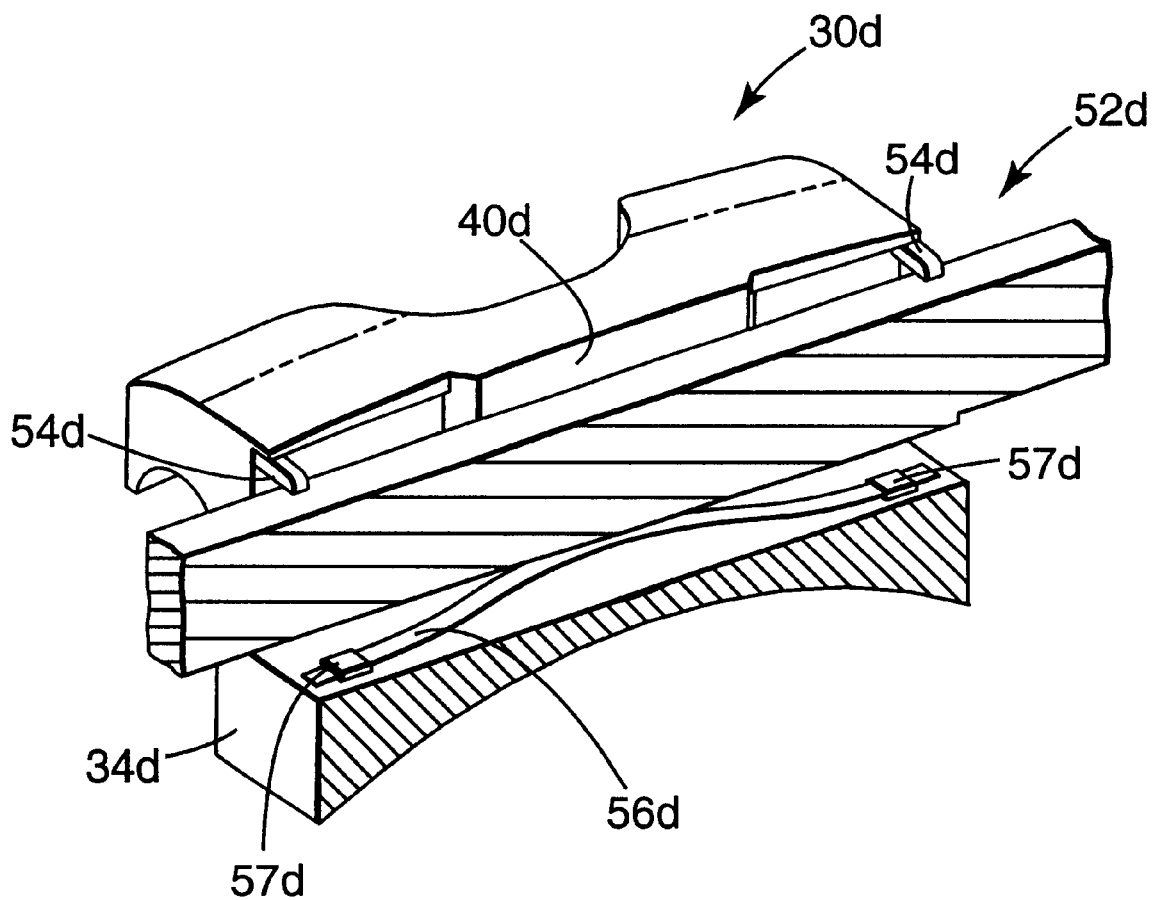
FIG. 9 is a view somewhat similar to FIG. 2 but showing an orthodontic appliance that is constructed in accordance with another embodiment of the invention.

An orthodontic appliance 30d according to another embodiment of the invention is illustrated in FIG. 9 in sectional view. The appliance 30d is similar to the appliance 30a, except for the difference as set out below.

The appliance 30d includes a latch 52d having a spring member 56d that is preferably made from an initially flat section of resilient metallic spring material. The spring member 56d has a mesial portion, a distal portion and a middle portion located between the mesial portion and the distal portion. Additionally, the spring member 56d is elongated and extends along the length of an archwire slot 40d of the appliance 30d.

The mesial portion and the distal portion of the spring member 56d are movably connected to a body 34d of the appliance 30d. In the embodiment illustrated, a pair of sleeves 57d are fixed to the body 34d, and each sleeve 57d receives either the mesial portion or the distal portion of the spring member 56d. However, alternative structures for connecting the spring member 56d to the body 34d may also be employed, including the provision of slots in the body 34d or headed pins connected to the body 34d that extend through slots in the mesial and distal portions.

The middle portion of the spring member 56d is normally located a distance spaced in a buccolabial direction from the mesial and distal portions, but can be moved in a lingual direction against the inherent bias of the spring member 56d when desired. For example, when an archwire is inserted into the archwire slot 40d, the middle portion of the spring member 56d can be shifted lingually a distance sufficient to enable the archwire to clear four arm portions 54d of the latch 52d, so that the arm portions 54d can return to their normally slot-closed position. Only two of the arm portions 54d are shown in FIG. 9, but it should be understood in this regard that the latch 52d has four arm portions 54d constructed and arranged in similar fashion to the arm portions 54a of the appliance 30a. Alternatively, the arm portions may be constructed differently (e.g., according to the other options described above).

The middle portion of the spring member 56d serves as a movable floor or tab that defines a lingual side of the archwire slot 40d. Once an archwire is received in the archwire slot 40d and the arm portions 54d have returned to their slot-closed position, the middle portion of the spring member 56d urges the archwire toward a position of engagement with the arm portions 54d (assuming that the selected archwire has a sufficient cross-sectional configuration to substantially fill the archwire slot 40d). The spring member 56d preferably engages the archwire during the course of treatment for active therapy in a central portion of the body 34d, and preferably engages the archwire in a location adjacent the parallel wall portions of the archwire slot 40d where precise control over movement of the appliance 30d and the associated tooth is provided.

An orthodontic appliance 30e according to another embodiment of the invention is depicted in FIGS. 10–13. The appliance 30e is essentially the same as the appliance 30a, except for the differences as described below.

The appliance 30e has a latch 52e for releasably retaining an archwire 50e (FIGS. 11–13) in an archwire slot 40e. The latch 52e has two pair of flexible arm portions 54e that are identical to the arm portions 54a. However, instead of an elongated, single spring member (such as spring member 56a or 56b) the latch 52e has two pair of spring members or tabs 55e that are located adjacent mesial and distal sides of a body 34e of the appliance 30e.

The tabs 55e are optionally similar in construction to the arm portions 54e or any of the other arm portions described above. For example, the tabs 55e may be made of a section of flexible round or rectangular wire material such as nitinol or stainless steel. The tabs 55e may be affixed to the body 34e by any suitable means, including drilling holes in the body 34e to receive a portion of the tabs 55e and then securing the tabs 55e in place by an interference fit, by welding or brazing, by fasteners or by an adhesive bond.

The tabs 55e have buccolabial wall portions that rest against the archwire 50e during treatment in use to define a lingual side of the archwire slot 40e. The tabs 55e also are movable in a lingual direction sufficiently to enable the archwire 50e to be latched into the archwire slot 40e when desired. FIG. 12 illustrates movement of the tabs 55e as the archwire 50e is placed into the archwire slot 40e. As shown, the tabs 55e deflect in a lingual direction and bend in an arc a distance sufficient to enable the archwire 50e to clear the opposed, facing ends of the arm portions 54e as the archwire 50e is pushed in a lingual direction. At that time, the arm portions 54e will spring back to their normal orientation to close the archwire slot 40e. The inherent bias of the tabs 55e to a normally straight configuration then functions to urge a buccolabial side of the archwire 50e into engagement with the lingual side of the arm portions 54e.

FIG. 11 is an illustration for exemplary purposes of the archwire 50e in the archwire slot 40e during the course of orthodontic treatment. As shown, the tabs 55e are normally straight and also serve to urge the archwire 50e in a buccolabial direction toward a position of contact with the arm portions 54e. The tabs 55e thus function to provide an active form of orthodontic treatment during the course of therapy.

FIG. 13 is an illustration of the appliance 30e as the archwire 50e is released from the archwire slot 40e. As shown, the arm portions 54e deflect outwardly to open the archwire slot 40e and enable the archwire 50e to disengage the appliance 30e. Preferably, and like the latch 52, the arm portions 54e of the latch 52e release the archwire 50e whenever the archwire 50e exerts a force in a generally buccolabial direction on the appliance 30e that exceeds a certain minimum value. Preferably, that minimum force is substantially less than about one-half of the force required in the same direction to debond the appliance 30e from the associated tooth.

As shown in the drawings, the space between the opposed, facing ends of the tabs 55e is less than the space between the opposed, facing ends of the arm portions 54e. Preferably, the space between the opposed, facing ends of the tabs 55e is sufficiently small so that those ends do not engage the occlusal and gingival sides of the archwire 50e when the archwire 50e has reached its limit of travel in a lingual direction. Such construction helps ensure that the tabs 55e will remain in engagement with the lingual side of the archwire 50e or its adjacent corners so that the tabs 55e can subsequently function to return the archwire 50e to the position shown in FIG. 11 in reliable fashion.

As further options, the arm portions 52e in FIGS. 10–13 as well as the arm portions 54b, 54c and 54d as shown in FIGS. 7–9 respectively can be made by bending a section of wire to a generally "U"-shaped configuration, where the bight of the "U" is substantially longer in length than the length of its legs. The bight is then fixed to the bracket body in such a manner that the legs project toward the archwire slot in an occlusal or gingival direction and present the arm portions. Optionally, the bight section can be received in a shallow groove of the appliance body adjacent a labial side of the archwire slot.

The tabs 55e as illustrated in FIGS. 10–13 may also be made according to the "U"-shaped configuration described in the preceding paragraph. Construction of the arm portions and tabs in this manner reduces the number of parts to be handled during manufacturing, and also avoids the need to insert arm portions or tabs into small holes of the body. As an additional option, the arm portions or the tabs made in such a manner may also be comprised of a stack of discreet, generally "U"-shaped sections in order to present a stacked array similar to the stacked sections 53a' illustrated in FIG. 6a.

Figure 14:
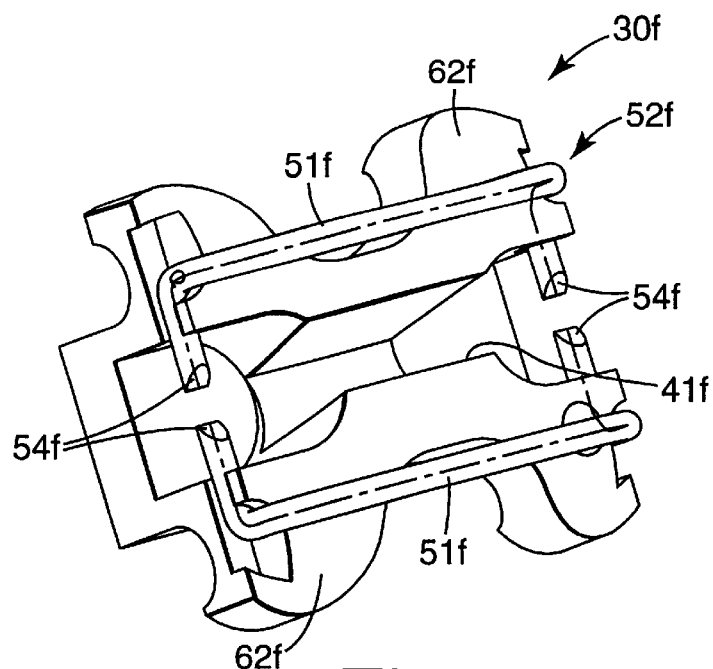
FIG. 14 is a perspective view of an orthodontic appliance according to another embodiment of the invention.

An orthodontic appliance 30f according to another embodiment of the invention is illustrated in FIG. 14. The appliance 30f is somewhat similar to the appliance 30e depicted in FIGS. 10–13 except for the differences noted below.

The appliance 30f includes a latch 52f that is comprised of a pair of opposed ligating members 51f, 51f. Each of the ligating members 51f has a generally "U"-shaped configuration in elevational view when viewed in a lingual direction. Each of the ligating members 51f has a pair of arm portions 54f, 54f, and the arm portions 54f of one ligating member 51f are directly opposed to the arm portions 54f of the opposite ligating member 51f. Other constructions, however, are also possible.

Each of the ligating members 51f is slidable along a generally occlusal-gingival reference axis is a direction toward and away from an archwire slot 40f of the appliance 30f. Preferably, each arm portion 54f has a chamfered outer end, such that the ligating members 54f slide away from each other to a slot-open position when an archwire (not shown) is inserted into the archwire slot 40f. As an alternative, however, the practitioner may elect to use a dental probe or ligature director to engage a middle portion of each ligating member 51f and slide the same outwardly in order to open the latch 52f.

Optionally, the appliance 30f may be provided with lingual archwire slot tabs somewhat similar to the tabs 55e illustrated in FIGS. 10–13. The tabs in such an instance are movable in a lingual direction sufficiently to enable the archwire to be inserted into the archwire slot 41f by deflecting the arm portions 54f in a lingual direction. In such construction, the arm portions 54f and the tabs function in a manner similar to the arm portions 54e and the tabs 55e described above. As another option, an elongated spring member (such as spring member 56 or 56d) may be provided in place of the tabs.

The appliance 30f also includes four tiewings 62f. Each of the tiewings 62f is similar to the tiewings 62 described in connection with the embodiment shown in FIG. 15, except that outer corners of the tiewings 62f have been constructed to provide for reception of the ligating members 51f and to enable limited sliding movement of the ligating members 51f when desired. The ligating members 51f may be made from a section of wire material such as stainless steel or nitinol.

Figure 15:
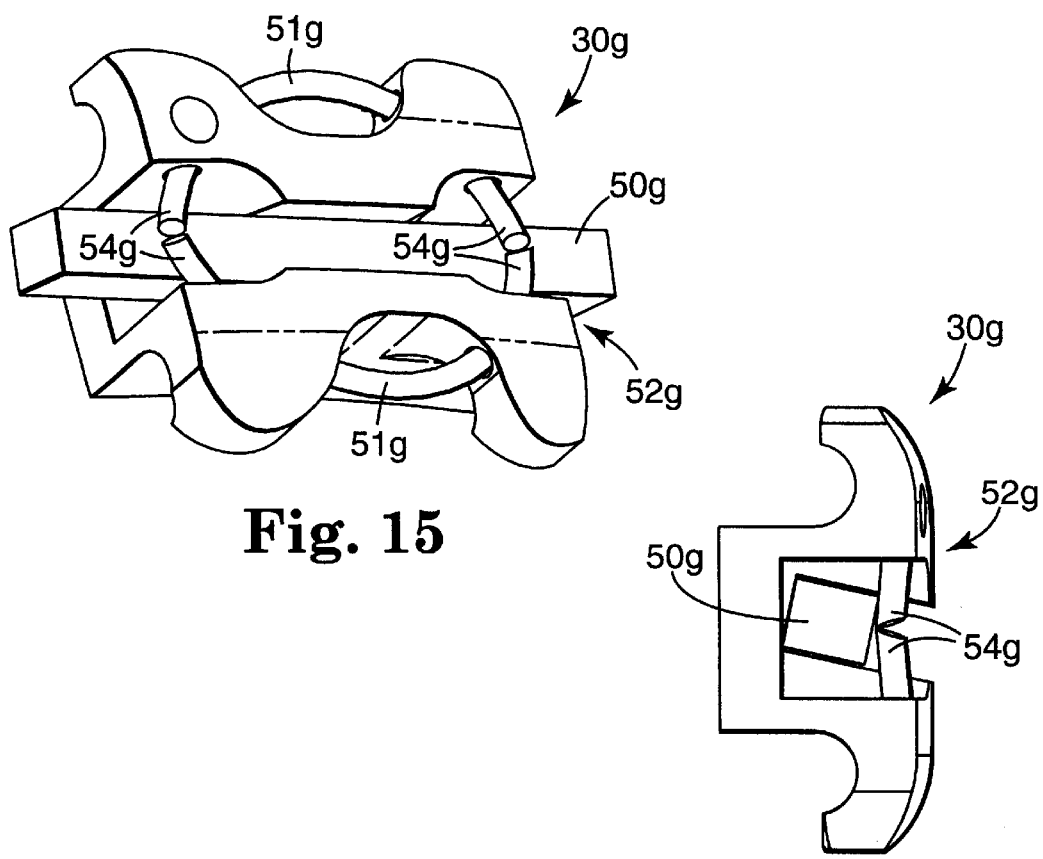
FIG. 15 is a perspective view of an orthodontic appliance constructed in accordance with still another embodiment of the invention, and additionally depicting an archwire that is received in an archwire slot of the appliance.
Figure 16:
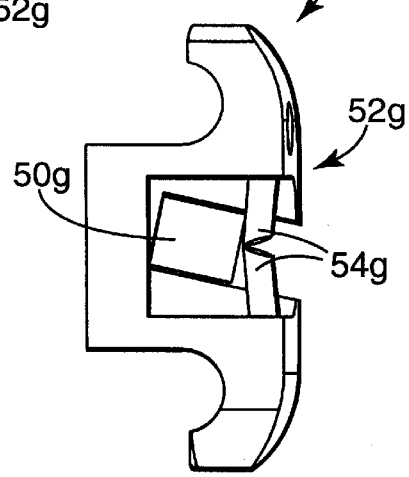
FIG. 16 is an end elevational view looking toward a mesial side of the appliance shown in FIG. 15 and showing the archwire in cross-section.

An orthodontic appliance 30g that is constructed according to yet another embodiment of the invention is shown in FIGS. 15 and 16 along with an archwire 50g that is received in an archwire slot of the appliance 30g. The appliance 30g is substantially the same as the appliance 30f, except for the differences as described below.

The appliance 30g has a pair of ligature members 51g that, in this embodiment, have an overall, generally semicircular configuration. Each of the ligature members 51g presents a pair of arm portions 54g that preferably have outer, chamfered ends. Each of the ligature members 51g extends through two passages that are located within tiewings of the appliance 30g.

The arm portions 54g move to admit the archwire 50g into the archwire slot of the appliance 30g. For example, a dental probe or ligature director may be inserted in the space between the tiewings on the occlusal or gingival side of the appliance 30g and the middle portion of the ligature members 51g, and then moved outwardly in order to move the arm portions 54g of that ligature member 51g into the passages. As another option, the arm portions 54g are deflected inwardly in a lingual direction as the archwire 50g is pushed into the archwire slot. The ligature member 51g may include crimps, stops or other structure to limit movement along the passages and avoid disengaging the appliance body. If desired, the appliance 30g may be provided with tabs similar to tabs 55e or with spring members similar to the spring members 56, 56d described above.

As another option, the ligature member 51g may be constructed to open the latch 52g whenever the middle portions of the ligature members 51g are squeezed together in directions toward the archwire slot. Optionally, the shape of the passages and/or the orientation of the passage may be modified to facilitate such opening movement. For example, the passages could be oriented in the occlusal-gingival directions, so that squeezing the middle portions together would cause the outer end portions 54g to retract into the passages. As another option, the passage could be elongated in mesial-distal directions in areas near the archwire slot relief areas, so that the arm portions 54g swing outwardly in distal directions when the middle portions are squeezed together. Any suitable hand instrument such as a pair of fine-tipped pliers may be used to squeeze the middle portions together. The latch 52g opens by deflection of the arm portions 54g outwardly as described above in connection with other embodiments.

Figure 17:
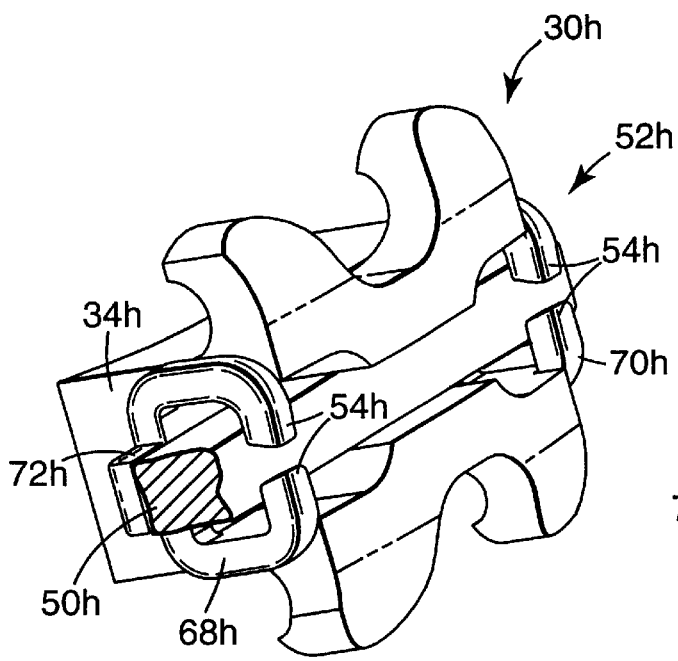
FIG. 17 is a perspective view of an orthodontic appliance constructed in accordance with still another embodiment of the invention along with an archwire received in an archwire slot of the appliance.
Figure 18:
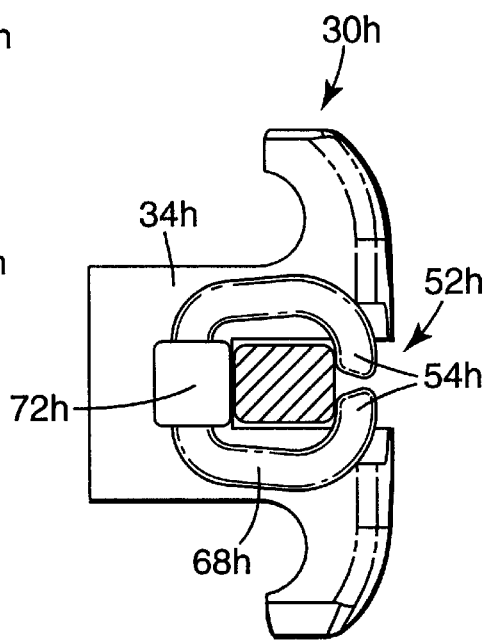
FIG. 18 is an end elevational view in partial cross-section looking toward a mesial side of the appliance of FIG. 17.

An orthodontic appliance 30h according to another embodiment of the invention is illustrated in FIGS. 17 and 18. The appliance 30h is essentially the same as the appliance 30 except for the differences described below.

The appliance 30*h* has a latch 52*h* that represents a variation of the earlier-described latches. The latch 52*h* comprises a mesial spring clip 68*h* and a distal spring clip 70*h*. The mesial spring clip 68*h* is fixed to a mesial side of a body 34*h* of the appliance 30*h*, while the distal spring clip 70*h* is fixed to a distal side of the appliance body 34*h*.

The clips 68*h*, 70*h* have an overall, generally "C"-shaped configuration and each includes a pair of arm portions 54*h* that extend toward each other. Preferably, each of the spring clips 69*h*, 70*h* is received in a channel of a sleeve 72*h*. The sleeve 72*h* is preferably fixed to a body 34*h* of the appliance 30*h* by a brazing or welding (including laser welding) process. The clip 68*h* and one sleeve 72*h* constitute a mesial assembly, and the clip 70*h* and the other sleeve constitute a distal assembly.

The sleeves 72*h* are an advantage in that the spring clips 68*h*, 70*h* may be made of a material that is difficult to weld or braze to the body 34*h*. For example, the clips 68*h*, 70*h* may be made of a resilient shape-memory alloy such as near-stoichiometric nitinol, while the body 34*h* may be made of an alloy of stainless steel. In that instance, the sleeve 72*h* may be also made of an alloy of stainless steel that can be readily welded or brazed to the body 34*h* according to conventional welding or brazing techniques. The sleeve 72*h* thus serves to couple the spring clips 68*h*, 70*h* to the body 34*h*.

The clips 68*h*, 70*h* including the arm portions 54*h* are sufficiently resilient to enable an archwire 50*h* to be inserted into an archwire slot by urging the archwire 50*h* in a lingual direction into the space within the confines of the clips 68*h*, 70*h*. As the archwire 50*h* engages the arm portions 54*h*, the clips 68*h*, 70*h* self-deflect and spread open a distance sufficient to enlarge the space between the arm portions 54*h* and allow the archwire 50*h* to pass through that space. Once the archwire 50*h* is received within the confines of the clips 68*h*, 70*h*, the clips 68*h*, 70*h* spring back to their normal orientation as shown in FIGS. 17 and 18 to retain the archwire 50*h* in the archwire slot.

The clips 68*h*, 70*h* including the arm portions 54*h* are sufficiently stiff to retain the archwire 50*h* in the archwire slot during the course of treatment so long as forces exerted by the archwire 50*h* on the appliance 30*h* are below a certain minimum value in a generally buccolabial direction (more particularly, in a direction opposite to the direction of insertion of the archwire 50*h* into the archwire slot). However, whenever the forces exerted by the archwire 50*h* on the appliance 30*h* in the same direction are greater than the minimum value, as might occur when unexpectedly high forces are encountered, the arm portions 54*h* deflect outwardly in a buccolabial direction and the clips 68*h*, 70*h* open to enable the archwire 50*h* to be released from the archwire slot. In this manner, the appliance 30*h* does not unintentionally debond from the tooth when unexpected, relatively high forces are encountered.

The shape of the outer ends of the arm portions 54*h* may be modified to enhance insertion or release of the archwire 50*h* as desired. For example, the outer, buccolabial corners of the arm portions 54*h* may be curved or tapered to facilitate spreading the clips 68*h*, 70*h* apart during insertion of the archwire 50*h* into the archwire slot. However, to ensure that the arm portions 54*h* do not spread apart until forces exerted by the archwire 50*h* exceed the minimum value, the facing end sections of the arm portions 54*h* may be cut at an angle or extended toward each other as needed.

Figure 19:
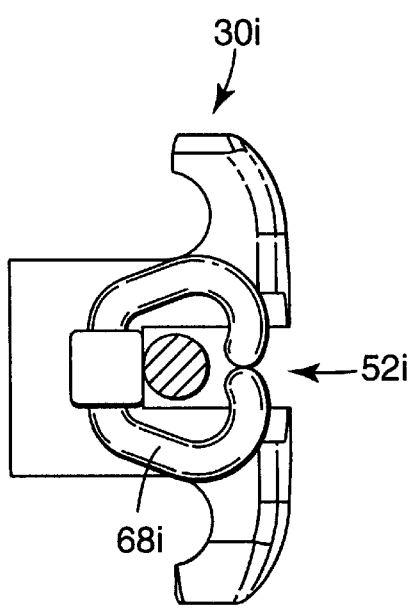
FIG. 19 is a view somewhat similar to FIG. 18 but showing an orthodontic appliance constructed in accordance with another embodiment of the invention.

An orthodontic appliance 30*i* according to yet another embodiment of the invention is illustrated in FIG. 19. The appliance 30*i* is essentially the same as the appliance 30*h* described above, except that the appliance 30*i* includes a latch 52*i* with a mesial spring clip 68*i* having a somewhat different shape than the mesial spring clip 68*h* shown in FIG. 18. The shape of the clip 68*i* may be an advantage in facilitating insertion of a smaller archwire 50*i* (such as an archwire having a circular cross-section as shown) in an archwire slot of the appliance 30*i*. The appliance 30*i* also has a distal spring clip that is not shown, but is essentially the same as the mesial spring clip 68*i*.

In the example shown in FIG. 19 the archwire is spaced from the clip 68*i* and as a result the appliance 30*i* provides passive orthodontic therapy. Optionally, the clip 68*i* can be constructed to engage the labial side of larger archwires, so that the appliance 30*i* in that instance provides active orthodontic therapy.

Figure 20:
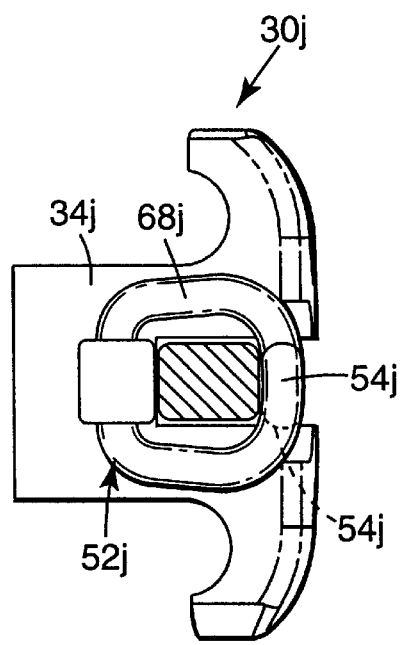
FIG. 20 is a view somewhat similar to FIG. 18 but showing an orthodontic appliance constructed in accordance with still another embodiment of the invention.

An orthodontic appliance 30*j* according to still another embodiment of the invention is illustrated in FIG. 20. The appliance 30*j* is essentially the same as the appliance 30*h* described in connection with FIGS. 17 and 18, except that the appliance 30*j* includes a latch 52*j* with a mesial spring clip 68*j* having a somewhat different shape than the mesial spring clip 68*h* shown in FIGS. 17 and 18. More particularly, the mesial spring clip 68*j* has a pair of arm portions 54*j* that overlap each other in directions along a mesial-distal reference axis and as shown by the dotted lines in FIG. 20. The appliance 30*j* has a distal spring clip that is not shown, but is identical to the mesial spring clip 68*j* and is optionally attached by a sleeve to a distal side of the appliance body.

Figure 21:
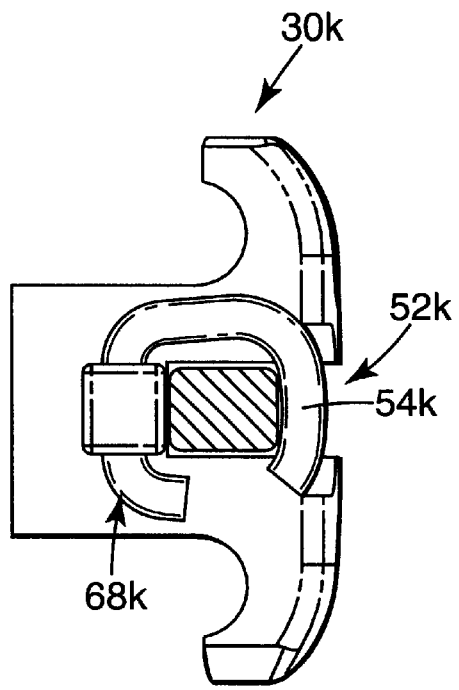
FIG. 21 is a view somewhat similar to FIG. 18 but showing an orthodontic appliance according to a further embodiment of the invention.

An orthodontic appliance 30*k* according to a further embodiment of the invention is illustrated in FIG. 21. The appliance 30*k* is essentially the same as the appliance 30*h* described above, except that the appliance 30*k* has a latch 52*k* with a mesial spring clip 68*k* having a generally "C"-shaped configuration. The mesial spring clip 68*k* presents only a single arm portion 54*k* that extends at least partially across, and preferably fully across the labial side of an archwire that is received in an archwire slot of the appliance 30*k*.

The appliance 30*k* also has a distal spring clip that is not illustrated in FIG. 21, but is essentially the same as the mesial spring clip 68*k*. The distal spring clip is optionally attached by a sleeve to a distal side of the body of the appliance 30*k*.

Figure 22:
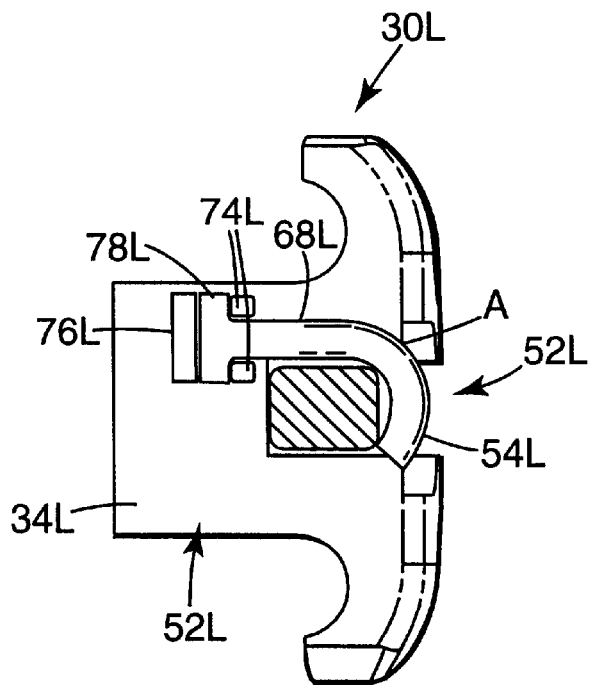
FIG. 22 is a view somewhat similar to FIG. 18 but showing an orthodontic appliance constructed according to an additional embodiment of the invention.

An orthodontic appliance 30L according to another embodiment of the invention is illustrated in FIG. 22. The appliance 30L is somewhat similar to the appliance 30*h*, except that the appliance 30L has a latch 52L that includes a mesial spring clip 68L having a generally overall "J"-shaped configuration. The mesial spring clip 68L also has only a single arm portion 54L that extends at least partially across, and preferably fully across a labial side of an archwire that is received in an archwire slot of the appliance 30L.

A bracket body 34L of the appliance 30L includes a pair of bosses 74L as well as a bar 76L. The bosses 74L and the bar 76L are preferably integrally connected with a body 34L of the appliance 30L and project outwardly in a mesial direction. The spring clip 68L has a lingual end portion 78L with a "T"-shaped configuration that fits snugly between the bosses 74L as well as the bar 76L in the manner depicted in FIG. 22.

Although not shown in the drawings, the appliance 30L includes a small mesial cap that covers the lingual end portion 74L of the mesial spring clip 68L. Preferably, the cap engages both of the bosses 78L as well as the bar 76L, and is secured to the bosses 74L and the bar 76L by a brazing operation, by a spot welding operation or the like. The cap, the bosses 74L and the bar 76L cooperate to securely fix the lingual end portion 78L of the mesial spring clip 68L to the mesial side of the appliance 30L.

The latch 52L also includes a distal spring clip that is not shown in the drawings, but is identical to the mesial spring clip 68L and is attached to the bracket body 34L in a similar manner. That is, the appliance 30L includes a pair of distally extending bosses and a distally extending bar that are connected to a distal side of the appliance 30L and are similar to the bosses 74L and the bar 76L respectively. Additionally, a cap is secured to the distal bosses and the distal bar in order to secure a lingual end portion of the distal spring clip to the distal side of the appliance body 34L.

Optionally, the spring clips of the appliances 30h-30L (including the spring clips 68h, 68L) are cut from a flat section of metallic stock material. Suitable metallic materials include shape memory alloys such as alloys of nitinol and beta-titanium. The spring clips may be cut from the stock material using a stamping, die cutting, chemical etching, EDM, laser cutting, or water jet cutting process. Advantageously, the clips and the sleeves of FIGS. 19 and 20 have mating, rectangular shapes in cross-sectional view so that the sleeves prevent pivotal movement of the clips relative to the appliance body about an occlusal-gingival axis.

As another option, the spring clips of the appliances, and particularly the spring clips of the appliances 30h, are cut from a section of tubing that is made from a shape memory alloy. Suitable shape memory alloys include alloys of nitinol and beta-titanium. The tubing is cut with a slot to form the arm portions (such as the arm portions 54h).

As an additional option, the spring clips, the bracket bodies or other structure of the appliances 30h-30L are provided with a section of material that limits the degree of bending of the clip. For example, the clip 68L may have a small, labially extending section near an outer corner at the location designated "A". When the arm portion 54L is bent outwardly to open the latch 52L, the labially extending section prevents undue bending of the arm portion 54L so that the likelihood of damaging the clip 68L is reduced. As another example, the tiewings could have a small protrusion extending outwardly along a mesial-distal reference axis in the path of the clip in order to function as a stop and limit outward movement of the clip when the clip is opened.

In the appliances shown in FIGS. 17–20, the clips can be spread apart to different orientations in order to accommodate wires having different cross-sectional shapes. The clips also have inherent memory to repeatedly spring back to a closed position, so that occlusal and gingival sides of the clips are in contact with or closely adjacent the occlusal and gingival sides of the archwire respectively. Such construction provides better control over movement of the associated tooth.

Additionally, the clips of the appliances shown in FIGS. 17–24 preferably have a shape that facilitates opening of the latch when the archwire is pushed against the clip in a lingual direction. For example, the labial side of the clips preferably extends at an angle relative to an occlusal-gingival reference axis, so that the clip or at least the arm portion of the clip tends to deflect in a lateral direction (such as in an occlusal or in a gingival direction) as the archwire is urged in a lingual direction in order to open the latch and admit the archwire into the archwire slot.

Figure 23:
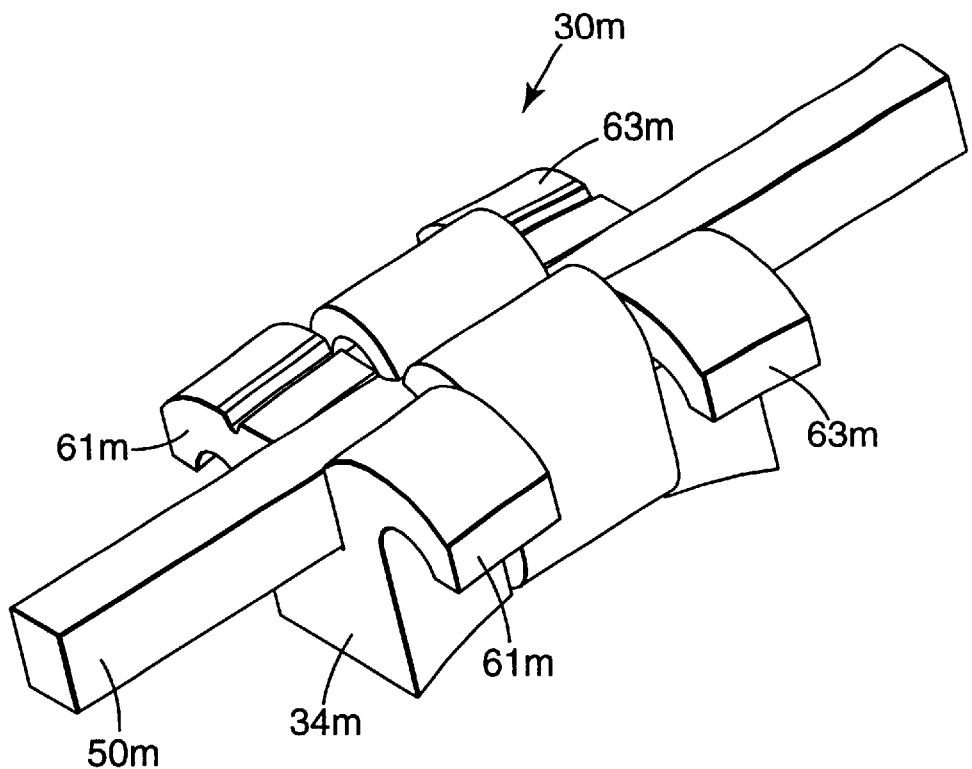
FIG. 23 is perspective view of an orthodontic appliance constructed according to yet another embodiment of the invention, along with an archwire that is received in an archwire slot of the appliance.
Figure 24:
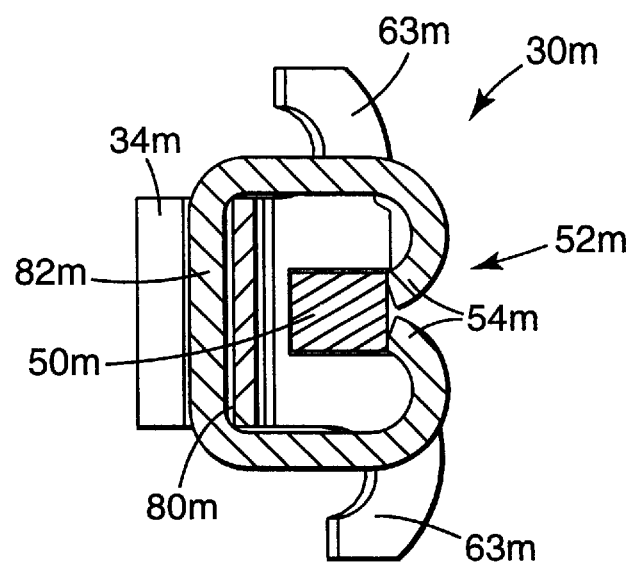
FIG. 24 is a cross-sectional view of the appliance and the archwire depicted in FIG. 23, and looking in a generally mesial-distal direction along a longitudinal axis of the archwire.

An orthodontic appliance 30m according to another embodiment of the invention is illustrated in FIGS. 23 and 24. The appliance 30m includes an appliance body 34m with a "twin tiewing" construction having mesial tiewings 61m that are spaced apart from distal tiewings 63m. The appliance body 34m also has a "vertical" channel 80m (FIG. 24) that is located lingually of an archwire slot of the appliance 30m and that extends in a generally occlusal-gingival direction.

The appliance 30m includes a latch 52m that is received in the space between the mesial tiewings 61m and the distal tiewings 63m. The latch 52m includes a lingual portion 82m that is received in the channel 80m. Although not shown in the drawings, the appliance 30m includes a base that is secured to a lingual side of the appliance body 34m, and the base captures the lingual portion 82m in the channel 80m in order to retain the latch 52m in secure connection to the body 34m.

The latch 52m includes a pair of arm portions 54m, each of which is shaped to engage a labial side of an archwire 50m when received in an archwire slot of the appliance 30m. Each arm portion 54m has a somewhat "C"-shaped configuration, although other shapes are also possible. The "C"-shaped configuration as illustrated in FIG. 24 is an advantage, in that the arm portions 54m laterally deflect in occlusal and gingival directions respectively when the practitioner attempts to insert the archwire 50m into the archwire slot.

The latch 52m may be made of a section of resilient material such as stainless steel or nitinol. Other aspects of the appliance 30m are similar to the features of the appliances described above.

Figure 25:
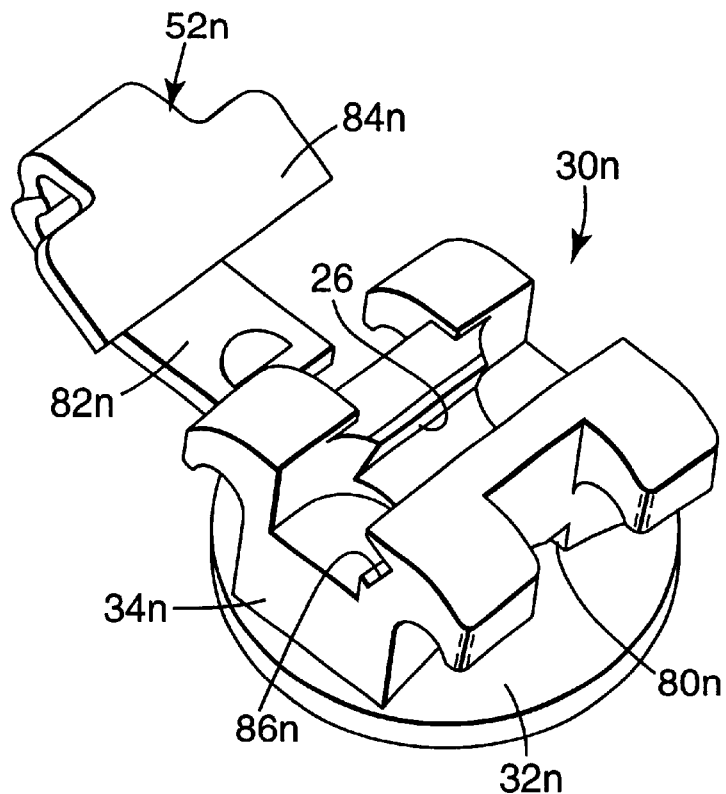
FIG. 25 is a perspective, exploded view of an orthodontic appliance that is constructed in accordance with another embodiment of the invention.
Figure 26:
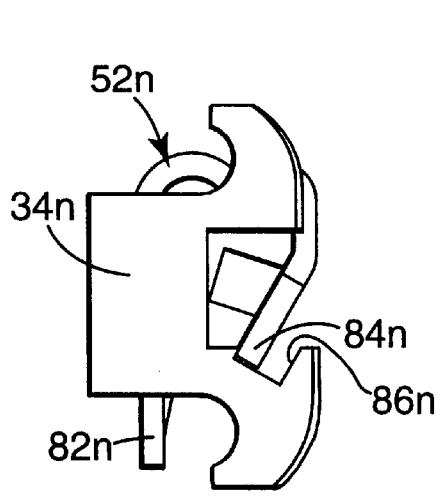
FIG. 26 is an end elevational view of the appliance shown in FIG. 25, wherein a latch of the appliance is illustrated in a slot-closed position.
Figure 27:
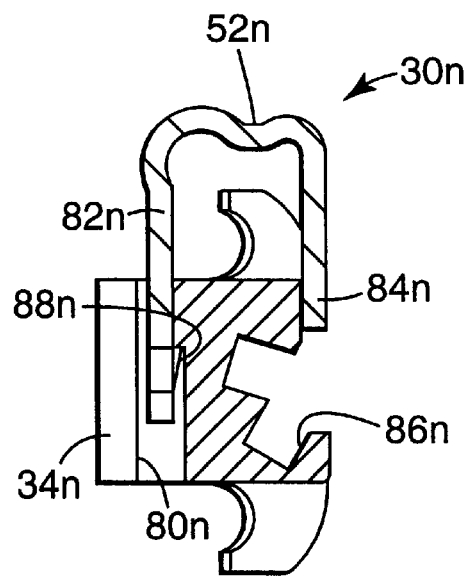
FIG. 27 is a cross-sectional view of the appliance shown in FIGS. 25 and 26, except that the latch has been moved to a slot-open position.

Another embodiment of the invention is shown in FIGS. 25–27, wherein an orthodontic appliance 30n according to the invention includes a bracket body 34n and a latch 52n. The latch 52n has a generally "U"-shaped configuration, and a lingual portion 82n of the latch 52n is received in a channel 80n (FIG. 27) of the appliance body 34n.

The appliance 30n is shown in exploded form in FIG. 25, where the latch 52n is separated from the appliance body 34n. FIGS. 26 and 27 illustrate the appliance 30n as it appears once the latch 52n has been assembled to the appliance body 34n.

The latch 52n is movable relative to the body 34n in a generally occlusal-gingival direction along the length of the channel 80n. In FIG. 26, the latch is shown in a slot-closed position wherein a labial end portion 84n of the latch 52n is received in an elongated cavity 86n.

In FIG. 27, the latch 52n is shown in a slot-open position that enables insertion or removal of an archwire from the archwire slot of the bracket. The lingual portion 82n of the latch 52n includes a protrusion 88n that engages a shoulder in the channel 80n to limit further movement of the latch 52n in an occlusal direction. As such, the protrusion 88n substantially prevents the latch 52n from unintentionally separating from the body 34n.

The appliance 30n also includes a base 32n that is fixed to the appliance body 34n by a brazing operation, by a tech-welding operation or by other suitable means. The base 32n is shown in FIG. 25 but is omitted in FIGS. 26 and 27. The base 32n serves to secure the appliance 30n to the patient's tooth surface, and also functions to capture the lingual portion 82n of the latch 52n in the channel 80n in order to retain the latch 52n in connected relationship to the body 34n.

The latch 52n is constructed so that the labial portion 84n is released from the cavity 86n and deflects outwardly in a labial direction whenever the archwire exerts a force on the latch 52n greater than a certain minimum value in a generally buccolabial direction that is substantially parallel with occlusal and gingival sides of the archwire slot. The minimum value is described above, and is significantly less than the force required in the same direction to debond the appliance 30n from the tooth. To this end, the length of the labial portion 84n that is received in the cavity 86n, and the geometry and bending strength of the latch 52h are selected so that the latch 52n reliably opens when the selected minimum value is exceeded. The latch 52n opens in this manner by outward bowing of the labial portion 84n and is ultimately released from the cavity 86n without movement of the latch 52n in an occlusal direction (i.e., without movement toward the orientation as shown in FIG. 27).

In other respects, the appliance 30n is similar to the orthodontic appliance described in applicant's pending application Ser. No. 09/276,060 filed Mar. 25, 1999 and entitled "SELF-LIGATING ORTHODONTIC BRACKET WITH ENHANCED ROTATION CONTROL". That application is incorporated by reference herein, and the reader is referred to that application for additional details and other optional features if desired.

An orthodontic appliance 30p according to another embodiment of the invention is illustrated in FIGS. 28 and 29. The appliance 30p includes a latch 52p that is pivotally connected to an appliance body 34p. As shown in FIG. 29, the latch 52p includes an occlusal end section or cross bar 90p that is received in passages of two cylindrical hinge sections 92p, one of which is shown in FIG. 29. Each of the hinge sections 92p is located lingually beneath a respective tiewings 62p.

The appliance body 34p includes an elongated, protruding catch 94p. The latch 32p includes a gingival end section that is curved to form a notch. When the latch 52p is in a closed position as illustrated in FIGS. 28 and 29, the notch engages the catch 94p and retains an archwire in an archwire slot of the appliance body 34p.

When the practitioner desires to open the latch 52p, the practitioner may place a dental probe, explorer or other fine-tipped hand instrument on the gingival portion of the latch 52p in order to deflect the gingival portion in a gingival direction and disengage the catch 94p. At that time, the latch 52p can be pivoted about the central axis of the hinge sections 92p in order to open the latch 52p and enable the archwire to be released from the archwire slot.

However, if the archwire exerts a force on the latch 52p of sufficient magnitude, the labial portion of the latch 52p will automatically disengage the catch 94p and allow the latch 52p to self-open. The latch 52p releases the archwire from the archwire slot whenever the archwire exerts a substantial force on the latch 52p so that the appliance 30p is not unintentionally debonded from the tooth. Preferably, the latch 52p opens whenever the force exerted by the archwire exceeds a certain minimum value as described above.

A variety of methods can be employed to ensure that the latch 52p opens whenever the archwire has exerted a force on the latch 52p of sufficient magnitude. For example, the shape of the notch of the occlusal portion of the latch 52p, as well as the shape of the catch 94p, may be altered as needed to vary the amount of force necessary to open the latch 52p. As another example, the material of the latch 52p may vary in composition or processed according to different conditions to ensure that the latch 52p consistently deforms whenever the desired minimum force of the archwire on the latch 52p has been exceeded.

As another alternative, the appliance 30p could be constructed so that the latch 52p is fixed on one end and bends when opened. Optionally, a lingual side of the latch could be fixed to a side of the appliance body, or within a lingual channel (not shown) of the body somewhat similar to the channel 80n shown in FIGS. 25–27. The opposite side of the latch in that instance would have a notch, groove, curve or some other shape adapted to releasably engage a cavity (such as cavity 86n), a protrusion or some other feature of the appliance.

An orthodontic appliance 30q according to another embodiment of the invention is illustrated in FIG. 30, and includes an appliance body 34q as well as a swingable latch 52q. In this embodiment, the latch 52q is pivotally connected to a tiewings 62q of the appliance body 34q.

The latch 52q includes an occlusal portion 96q that is releasably received over an occlusal tiewing 62q of the appliance body 34q. The occlusal portion 92q and the outer end of the occlusal tiewing 62q preferably have mating, curved shapes. When the latch 52q is in the position illustrated in FIG. 30, the latch 52q serves to retain an archwire 50q in an archwire slot of the appliance body 34q.

The latch 52q and the appliance body 34q are constructed to enable the latch 52q to move to a slot-open position whenever the force exerted by the archwire 50q in a buccolabial direction exceeds a certain minimum value. Preferably, the minimum value is the same as the minimum values described above. The latch 52q may also be manually opened by use of a dental probe, explorer or other hand instruments to deflect and disengage the occlusal portion 92q from the occlusal tiewings 62q.

Figure 31:
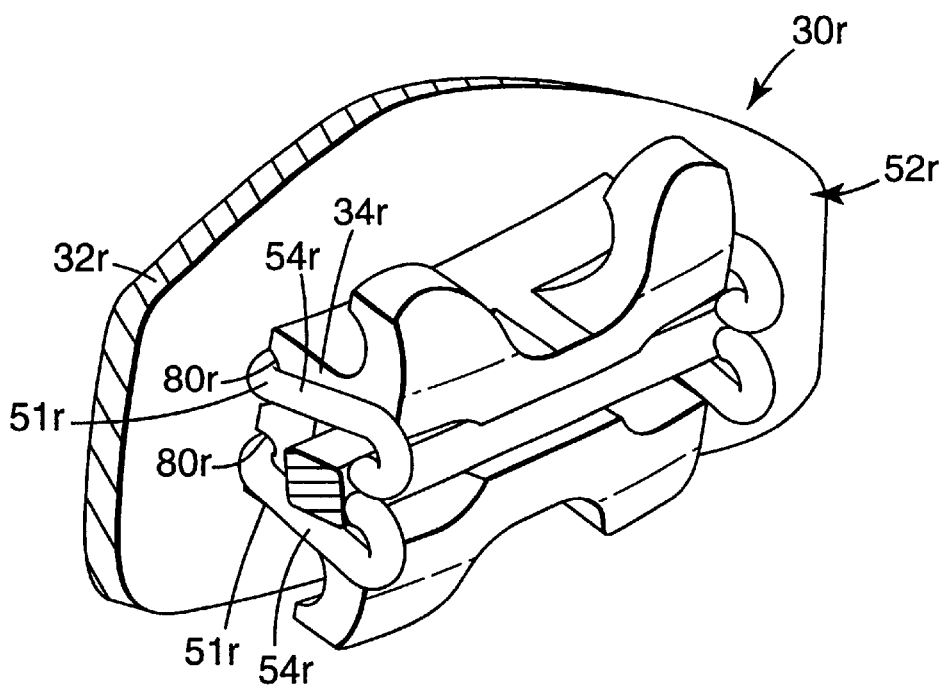
FIG. 31 is a perspective view of an orthodontic appliance constructed in accordance to a further embodiment of the invention.

FIG. 31 is an illustration of an orthodontic appliance 30r according to another embodiment of the present invention. As shown, the appliance 30r has a body 34r that is preferably identical to the body 34, except that the body 34r includes two, spaced-apart channels 80r along its lingual side. A latch 52r includes two ligating members 51r, 51r that have a generally "U"-shaped configuration when viewed along an occlusal-gingival reference axis. Each ligating member 51r has on opposite sides a pair of outer arm portions 54r, each of which includes a loop-shaped section.

The appliance 30r also includes a base 32r that, once fixed to the appliance body, serves to secure a lingual portion of the ligating members 51r in the channels 80r. Optionally, the channels 80r and the ligating members 51r have mating, rectangular or square cross-sectional configurations when viewed in directions perpendicular to their longitudinal axis, so that the lingual portion of each ligating member 51r will not pivot within the channels 80r. Optionally, the base 32r and the lingual portions of both ligating members 80r are welded, brazed or otherwise fixed to the appliance body in order to prevent pivotal movement of the ligating members 51r within the channels 80r.

The ligating members 51r are preferably made from resilient wire stock such as the stainless steel wires or wires made of the shape memory alloys described above. To open the latch 52r, the arms portions 54r spread apart and swing away from each other in opposite directions along mesial and distal sides of the appliance body. The latch 52r self-opens to admit or release an archwire whenever forces exerted by the archwire on the loop sections exceeds certain values, similar to the latches described above. The loop sections may be used to receive a hand instrument (such as a probe or fine tips of pliers) for manual opening of the latch 52r when desired.

Figure 32:
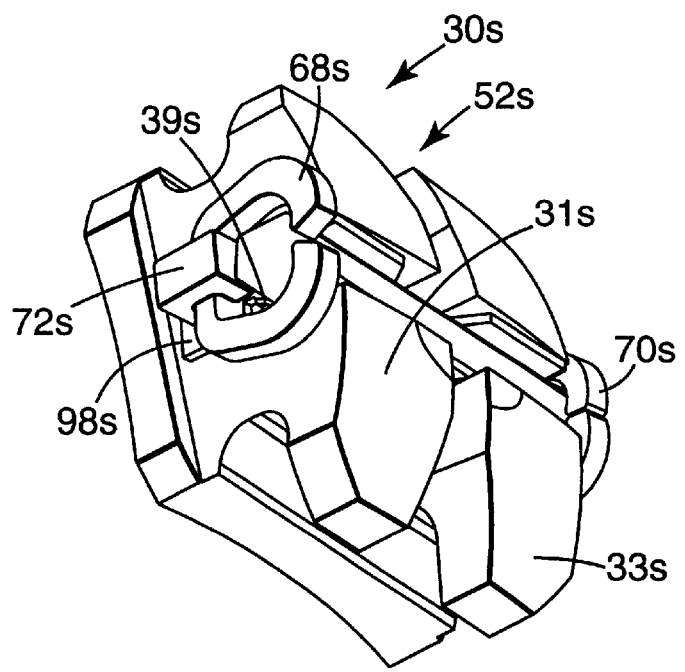
FIG. 32 is a perspective view of an orthodontic appliance that is constructed in accordance with still another embodiment of the invention.

An orthodontic appliance 30s that is constructed according to another embodiment of the invention is depicted in FIG. 32. The appliance 30s includes aesthetic ceramic mesial and distal body sections 31s, 33s respectively and is somewhat similar to the appliances described in U.S. Pat. Nos. 5,439,379 and 5,366,372, both of which are expressly incorporated by reference herein. The appliance 30s also includes an metallic archwire slot liner 39s that defines an archwire slot 40s. Examples of suitable materials and methods of constructing the archwire slot liner 39s, as well as examples of suitable methods for attaching the archwire slot liner 39s to the body sections 31s,33s are described in U.S. Pat. Nos. 5,358,402 and 5,380,196, both of which are also expressly incorporated by reference herein.

The archwire slot liner 39s includes a mesial segment 98s that extends along a mesial side of the mesial body section 31s in parallel relationship. Preferably, the mesial segment 98s is secured to the mesial side of the body section 31s by use of the methods described in U.S. Pat. Nos. 5,358,402 and 5,380,196. The mesial segment 98s serves as a mount for receiving a sleeve 72s of a latch 52s. The sleeve 72s is similar to the sleeve 72h described above and serves to couple a mesial spring clip 68h to the mesial body section 31s.

The clip 68s that is illustrated for exemplary purposes in FIG. 32 is similar to the clip 68h, although other clips such as the clips 68i–68L could alternatively be used. Additionally, the latch 52s includes a distal clip 70s that is secured by a distal sleeve to a distal segment of the archwire slot liner 39s. The distal sleeve and distal segment of the archwire slot liner 39s are not shown, but are similar to the mesial sleeve 72s and mesial segment 98s respectively. The latch 52s operates similarly to the latches described in the other embodiments above.

Optionally, the appliances according to the invention, and particularly the appliances 30n, 30p and 30q illustrated in FIGS. 25–30, may be provided with a selfreleasing latch that is movable from a slot-open position to either a first closed position or a second closed position. In the first closed position of the latch, the latch engages an archwire with sufficient force to provide active orthodontic therapy. In the second closed position, the effective labial-lingual dimension of the archwire slot is somewhat greater than the overall labial-lingual dimension of the archwire such that the bracket provides passive orthodontic therapy. Further details of dual mode orthodontic brackets are described in applicant's pending U.S. patent application Ser. No. 09/218,929 filed Dec. 22, 1998 and entitled "DUAL MODE SELF LIGATING ORTHODONTIC BRACKET".

In all of the embodiments described above, the latch is made of a material having sufficient inherent memory to self-return to its original shape once pressure on the latch has been relieved. As a result, the latch does not permanently deform and can be used repeatedly, even in instances where the archwire has opened the latch a number of times during treatment. Other aspects of the latches 52a–52s or other features of the appliances 30a–30s that are not described in detail are similar to corresponding aspects of the latch 52 or features of the appliance 30.

Those skilled in the art may recognize that a number of modifications and additions are possible to the presently preferred embodiments that are described in detail above. For example, the latches as mentioned above may be utilized with a variety of other types of orthodontic appliances including single tiewing brackets, three wing brackets and the like. Alternatively, the tiewings may be omitted if desired.

Additionally, the appliances may be made of materials other than metal, including ceramics, plastics and the like. Optionally, the archwire slots of the appliances may include an archwire slot liner or may be coated with a material to facilitate movement of the appliance along the archwire. A number of other variations are also possible. Accordingly, the invention should not be deemed limited to the specific embodiments described above, but instead only by a fair scope of the claims that follow along with their equivalents.

We claim:

1. An orthodontic appliance comprising:
    a base for bonding an appliance to a tooth;
    a body extending from the base;
    an archwire slot extending across the body in a generally mesial-distal direction; and
    a latch connected to the body for releasably retaining an archwire in the archwire slot, wherein the latch releases the archwire from the archwire slot in a generally buccolabial direction whenever the archwire exerts a force greater than about 2.3 kg in the same direction on the appliance.

2. An orthodontic appliance according to claim 1 wherein the latch releases the archwire from the archwire slot whenever the archwire exerts a force greater than about 1.4 kg on the appliance.

3. An orthodontic appliance according to claim 1 where in the latch releases the archwire from the archwire slot whenever the archwire exerts a force greater than about 0.7 kg on the appliance.

4. An orthodontic appliance according to claim 1 wherein the latch is movable to a slot-open position to enable passage of the archwire in the archwire slot.

5. An orthodontic appliance according to claim 1 wherein the latch is movable to the slot-open position by pressing the archwire against the latch in a generally lingual direction.

6. An orthodontic appliance according to claim 1 wherein the latch includes at least one arm portion that is movable outwardly in a generally buccolabial direction to release the archwire.

7. An orthodontic appliance according to claim 6 wherein each arm portion is also movable inwardly in a generally lingual direction to admit the archwire into the archwire slot.

8. An orthodontic appliance according to claim 1 wherein the archwire slot includes a lingual side that is defined by wall portions that are movable relative to the body.

9. An orthodontic appliance according to claim 1 wherein the latch includes a mesial clip and a distal clip, and wherein each of the clips have an overall, generally "C"-shaped configuration.

10. An orthodontic appliance according to claim 9 wherein the body includes a mesial side and a distal side, and wherein the mesial clip is secured to the mesial side and the distal clip is secured to the distal side.

11. An orthodontic appliance according to claim 1 wherein the latch is slidable in a generally occlusal-gingival direction in order to open or close the archwire slot.

12. An orthodontic appliance according to claim 1 wherein the latch is pivotally movable relative to the body in order to open or close the archwire slot.

13. An orthodontic appliance according to claim 1 wherein the body includes a channel extending in a generally mesial-distal direction, and wherein the latch includes a lingual portion that is received in the channel.

14. An orthodontic appliance according to claim 1 wherein the body includes a channel extending in a generally occlusal-gingival direction, and wherein the latch includes a lingual portion that is received in the channel.

15. An orthodontic appliance according to claim 1 wherein the appliance includes an archwire slot liner with a mesial segment and a distal segment, and wherein the latch includes a mesial clip coupled to the mesial segment and a distal clip coupled to the distal segment.

16. An orthodontic appliance comprising:
   a base for bonding the appliance to a tooth;
   a body extending from the base;
   an archwire slot extending across the body in a generally mesial-distal direction; and
   a latch connected to the body for releasably retaining an archwire in the archwire slot, wherein the latch releases the archwire from the archwire slot whenever the archwire exerts a force in a generally buccolabial direction on the appliance that exceeds a certain minimum value, and wherein the minimum value is less than about one-half of the force required in the same direction to debond the appliance from the tooth.

17. An orthodontic appliance according to claim 16 wherein the latch is movable to a slot-open position to enable passage of the archwire in the archwire slot.

18. An orthodontic appliance according to claim 17 wherein the latch when in the slot-open position has a different orientation relative to the body than the orientation of the latch when the latch releases the archwire from the archwire slot.

19. An orthodontic appliance according to claim 17 wherein the latch is movable to the slot-open position by pressing the archwire against the latch in a generally lingual direction.

20. An orthodontic appliance according to claim 16 wherein the appliance is an orthodontic bracket or buccal tube.

21. An orthodontic appliance according to claim 16 wherein the appliance includes at least one tiewing.

22. An orthodontic appliance according to claim 16 wherein the latch includes at least one arm portion that is movable outwardly in a generally buccolabial direction to release the archwire.

23. An orthodontic appliance according to claim 22 wherein each arm portion is also movable inwardly in a generally lingual direction to admit the archwire into the archwire slot.

24. An orthodontic appliance according to claim 23 wherein the body includes at least one shoulder extending over each arm portion.

25. An orthodontic appliance according to claim 16 wherein the archwire slot includes an occlusal side and a gingival side that are defined by wall portions fixed to the body.

26. An orthodontic appliance according to claim 16 wherein the archwire slot includes a lingual side that is defined by wall portions that are immovable relative to the body.

27. An orthodontic appliance according to claim 16 wherein the archwire slot includes a lingual side that is defined by wall portions that are movable relative to the body.

28. An orthodontic appliance according to claim 27 wherein the wall portions are part of movable tabs that are connected to the body.

29. An orthodontic appliance according to claim 28 wherein the tabs are resilient.

30. An orthodontic appliance according to claim 27 wherein the wall portions are part of an elongated spring member that extends in a direction along the length of the archwire slot.

31. An orthodontic appliance according to claim 16 wherein the latch includes a mesial clip and a distal clip, and wherein each of the clips have an overall, generally "C"-shaped configuration.

32. An orthodontic appliance according to claim 31 wherein the body includes a mesial side and a distal side, and wherein the mesial clip is secured to the mesial side and the distal clip is secured to the distal side.

33. An orthodontic appliance according to claim 16 wherein the body includes a channel extending in a generally occlusal-gingival direction, and wherein the latch includes a lingual portion that is received in the channel.

34. An orthodontic appliance according to claim 16 wherein the body includes a channel extending in a generally mesial-distal direction, and wherein the latch includes a lingual portion that is received in the channel.

35. An orthodontic appliance according to claim 16 wherein the appliance includes an archwire slot liner with a mesial segment and a distal segment, and wherein the latch includes a mesial clip coupled to the mesial segment and a distal clip coupled to the distal segment.

36. An orthodontic appliance comprising:
   a base for bonding the appliance to a tooth;
   a body extending from the base;
   an archwire slot extending across the body in a generally mesial-distal direction and having an occlusal side, a gingival side, a buccolabial side and a lingual side; and
   a latch connected to the body for releasably retaining an archwire in the archwire slot, wherein the latch is movable to a slot-open position to enable passage of the archwire into the slot by pressing the archwire against the latch in a direction toward the lingual side of the archwire slot, wherein the occlusal side and the gingival side of the archwire slot are stationary relative to each other as the latch is moved to the slot-open position, and wherein the latch includes at least one clip extending along the occlusal side, the gingival side and the lingual side of the archwire slot with opposed arm portions that extend toward each other across a buccolabial side of the archwire slot, the at least one clip comprising a shape-memory alloy.

37. An orthodontic appliance according to claim 36 wherein the occlusal side and the gingival side of the archwire slot are defined by wall portions fixed to the body.

38. An orthodontic appliance according to claim 36 wherein the archwire slot includes a lingual side that is defined by wall portions that are immovable relative to the body.

39. An orthodontic appliance according to claim 36 wherein the archwire slot includes a lingual side that is defined by wall portions that are movable relative to the body.

40. An orthodontic appliance according to claim 39 wherein the wall portions are part of movable tabs that are connected to the body.

41. An orthodontic appliance according to claim 40 wherein the tabs are resilient.

42. An orthodontic appliance according to claim 40 wherein the tabs move in a generally lingual direction as the archwire passes into the slot.

43. An orthodontic appliance according to claim 39 wherein the wall portions are part of an elongated spring member that extends in a direction along the length of the archwire slot.

44. An orthodontic appliance according to claim 43 wherein the spring member has a mesial portion, a distal portion and a middle portion located between the mesial portion and the distal portion, and wherein the middle portion is located buccolabially of the mesial portion and the distal portion.

45. An orthodontic appliance according to claim 43 wherein the spring member has a mesial portion, a distal portion and a middle portion located between the mesial portion and the distal portion, and wherein the middle portion is located lingually of the mesial portion and the distal portion.

46. An orthodontic appliance according to claim 36 wherein the latch includes at least one arm portion that is movable outwardly in a generally buccolabial direction to release the archwire.

47. An orthodontic appliance according to claim 46 wherein each arm portion is also movable inwardly in a generally lingual direction to admit the archwire into the archwire slot.

48. An orthodontic appliance according to claim 36 wherein the body includes a channel extending in a generally occlusal-gingival direction, and wherein the latch includes a lingual portion that is received in the channel.

49. An orthodontic appliance according to claim 36 wherein the body includes a channel extending in a generally mesial-distal direction, and wherein the latch includes a lingual portion that is received in the channel.

50. An orthodontic appliance comprising:
a base for bonding the appliance to a tooth;
a body extending from the base;
an archwire slot extending across the body in a generally mesial-distal direction and having an occlusal side, a gingival side and a lingual side; and
a latch connected to the body for releasably retaining an archwire in the archwire slot, wherein the latch is movable to a slot-open position to enable passage of the archwire into the slot by pressing the archwire against the latch in a direction toward the lingual side of the archwire slot, and wherein the occlusal side and the gingival side of the archwire slot are stationary relative to each other as the latch is moved to the slot-open position,
wherein the latch moves to release the archwire whenever the archwire exerts a force in a generally buccolabial direction on the appliance that exceeds a certain minimum value, and wherein the minimum value is less than about one-half of the force required in the same direction to debond the appliance from the tooth.

51. An orthodontic appliance comprising:
a base for bonding the appliance to a tooth;
a body extending from the base;
an archwire slot extending across the body in a generally mesial-distal direction and having an occlusal side, a gingival side and a lingual side; and
a latch connected to the body for releasably retaining an archwire in the archwire slot, wherein the latch is movable to a slot-open position to enable passage of the archwire into the slot by pressing the archwire against the latch in a direction toward the lingual side of the archwire slot, and wherein the occlusal side and the gingival side of the archwire slot are stationary relative to each other as the latch is moved to the slot-open position,
wherein the latch releases the archwire from the archwire slot in a generally buccolabial direction whenever the archwire exerts a force greater than about 2.3 kg in the same direction on the appliance.

52. An orthodontic appliance comprising:
a base for bonding the appliance to a tooth;
a body extending from the base;
an archwire slot extending across the body in a generally mesial-distal direction and having an occlusal side, a gingival side and a lingual side; and
a latch connected to the body for releasably retaining an archwire in the archwire slot, wherein the latch is movable to a slot-open position to enable passage of the archwire into the slot by pressing the archwire against the latch in a direction toward the lingual side of the archwire slot, and wherein the occlusal side and the gingival side of the archwire slot are stationary relative to each other as the latch is moved to the slot-open position,
wherein the appliance includes an archwire slot liner with a mesial segment and a distal segment, and wherein the latch includes a mesial clip coupled to the mesial segment and a distal clip coupled to the distal segment.

53. An orthodontic appliance comprising:
a base for bonding the appliance to a tooth;
a body extending from the base;
an archwire slot extending across the body in a generally mesial-distal direction and having an occlusal side, a gingival side and a lingual side; and
a latch connected to the body for releasably retaining an archwire in the archwire slot, wherein the latch is movable to a slot-open position to enable passage of the archwire into the slot by pressing the archwire against the latch in a direction toward the lingual side of the archwire slot, wherein the lingual side of the archwire slot is movable in a generally lingual direction as the archwire is pressed into the archwire slot, wherein the latch moves to release the archwire whenever the archwire exerts a force in a generally buccolabial direction on the appliance that exceeds a certain minimum value, and wherein the minimum value is less than about one-half of the force required in the same direction to debond the appliance from the tooth.

54. An orthodontic appliance according to claim 53 wherein the lingual side of the archwire slot is defined by movable wall portions that are biased in a generally buccolabial direction.

55. An orthodontic appliance according to claim 53 wherein the occlusal side and the gingival side of the archwire slot are immovable relative to each other and extend in parallel relationship.

56. An orthodontic appliance comprising:
a base for bonding the appliance to a tooth;
a body extending from the base;
an archwire slot extending across the body in a generally mesial-distal direction and having an occlusal side, a gingival side and a lingual side; and
a latch connected to the body for releasably retaining an archwire in the archwire slot, wherein the latch is movable to a slot-open position to enable passage of the archwire into the slot by pressing the archwire against the latch in a direction toward the lingual side of the archwire slot, and wherein the lingual side of the archwire slot is movable in a generally lingual direction as the archwire is pressed into the archwire slot,
wherein the latch releases the archwire from the archwire slot in a generally buccolabial direction whenever the archwire exerts a force greater than about 2.3 kg in the same direction on the appliance.

57. An orthodontic appliance comprising:
a base for bonding the appliance to a tooth;
a body extending from the base and having a mesial side and a distal side;

an archwire slot extending across the body in a generally mesial-distal direction; and a latch movable between a slot-closed position for retaining an archwire in the archwire slot and a slot-open position for releasing the archwire from the archwire slot, wherein the latch comprises a mesial clip that is located mesially of the mesial side of the body and a distal clip that is located distally of the distal side of the body, wherein the appliance includes a mesial channel and a distal channel that receive the mesial clip and the distal clip respectively, wherein each clip is made of a shape-memory alloy, and wherein the body is made of a material different than the shape-memory alloy.

58. An orthodontic appliance according to claim 57 wherein each clip has an overall, generally "C"-shaped configuration.

59. An orthodontic appliance comprising:

a base for bonding the appliance to a tooth;

a body extending from the base and having a mesial side and a distal side;

an archwire slot extending across the body in a generally mesial-distal direction; and a latch movable between a slot-closed position for retaining an archwire in the archwire slot and a slot-open position for releasing the archwire from the archwire slot, wherein the latch comprises a mesial clip that is located mesially of the mesial side of the body and a distal clip that is located distally of the distal side of the body, wherein each clip includes at least one arm portion that is movable in a certain direction to release the archwire whenever the archwire exerts a force in a generally buccolabial direction on the appliance that exceeds a certain minimum value, and wherein the minimum value is less than about one-half of the force required in the same direction to debond the appliance from the tooth.

60. An orthodontic appliance according to claim 59 wherein each arm portion is also movable in a direction opposite of the certain direction to admit the archwire into the archwire slot.

61. An orthodontic appliance according to claim,wherein the latch releases the archwire from the archwire slot in a generally buccolabial direction whenever the archwire exerts a force greater than about 2.3 kg in the same direction on the appliance.

62. An orthodontic appliance comprising:

a base for bonding the appliance to a tooth;

a body extending from the base and having a mesial side and a distal side;

an archwire slot extending across the body in a generally mesial-distal direction; and a latch movable between a slot-closed position for retaining an archwire in the archwire slot and a slot-open position for releasing the archwire from the archwire slot, wherein the latch comprises a mesial clip that is located mesially of the mesial side of the body and a distal clip that is located distally of the distal side of the body, wherein the appliance includes an archwire slot liner with a mesial segment and a distal segment, and wherein the latch includes a mesial clip coupled to the mesial segment and a distal clip coupled to the distal segment.

63. An orthodontic appliance comprising:

a base for bonding the appliance to a tooth;

a body extending from the base;

an archwire slot extending across the body in a generally mesial-distal direction; and a latch movable between a slot-closed position for retaining an archwire in the archwire slot and a slot-open position for releasing the archwire from the archwire slot, wherein the latch comprises at least one assembly of a sleeve and a resilient clip extending through the sleeve, and wherein each sleeve is fixed to the body.

64. An orthodontic appliance according to claim 63 wherein the body includes a mesial side and a distal side, and wherein the latch comprises a mesial clip that is located mesially of the mesial side and a distal clip that is located distally of the distal side.

65. An orthodontic appliance according to claim 64 wherein the latch comprises a mesial sleeve that is fixed to the mesial side of the body and a distal sleeve that is fixed to the distal side of the body, and wherein the mesial clip extends through the mesial sleeve and the distal clip extends through the distal sleeve.

66. An orthodontic appliance according to claim 65 wherein each clip includes at least one arm portion that is movable outwardly in a generally buccolabially direction to release the archwire whenever the archwire exerts a force in a generally buccolabially direction on the appliance that exceeds a certain minimum value, and wherein the minimum value is less than the force required in the same direction to debond the appliance from the tooth.

67. An orthodontic appliance according to claim 66 wherein each arm portion is also movable inwardly in a generally lingual direction to admit the archwire into the archwire slot.

68. An orthodontic appliance according to claim 63 wherein each clip is made of a shape-memory alloy.

69. An orthodontic appliance according to claim 63 wherein the latch releases the archwire from the archwire slot in a generally buccolabial direction whenever the archwire exerts a force greater than about 2.3 kg in the same direction on the appliance.

70. An orthodontic appliance according to claim 63 wherein the appliance includes an archwire slot liner with a mesial segment and a distal segment, and wherein the latch includes a mesial clip coupled to the mesial segment and a distal clip coupled to the distal segment.

* * * * *

UNITED STATES PATENT AND TRADEMARK OFFICE
CERTIFICATE OF CORRECTION

PATENT NO.    : 6,302,688 B1                                                 Page 1 of 1
DATED         : October 16, 2001
INVENTOR(S)   : Jordan, Russell A.

It is certified that error appears in the above-identified patent and that said Letters Patent is hereby corrected as shown below:

Column 15,
Line 54, "is" should read -- in --.

Column 22,
Line 59, "sel-fopens" should read -- self-opens --.

Column 29,
Line 43, "claim," should read -- claim 60, --.

Signed and Sealed this

Twenty-ninth Day of October, 2002

*Attest:*

*Attesting Officer*

JAMES E. ROGAN
*Director of the United States Patent and Trademark Office*